(12) United States Patent
Chen et al.

(10) Patent No.: US 12,098,153 B2
(45) Date of Patent: Sep. 24, 2024

(54) **SMALL MOLECULE INHIBITORS TARGETING *CLOSTRIDIOIDES DIFFICILE* SPORULATION**

(71) Applicant: UNIVERSITY OF SOUTH FLORIDA, Tampa, FL (US)

(72) Inventors: Yu Chen, Tampa, FL (US); Michael Sacco, Tampa, FL (US); James Leahy, Tampa, FL (US); Elena Bray, Tampa, FL (US); Xingmin Sun, Tampa, FL (US); Xiujun Zhang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/376,525

(22) Filed: Oct. 4, 2023

(65) Prior Publication Data
US 2024/0051959 A1    Feb. 15, 2024

Related U.S. Application Data

(63) Continuation of application No. 17/850,650, filed on Jun. 27, 2022, now Pat. No. 11,814,385.

(60) Provisional application No. 63/202,834, filed on Jun. 25, 2021.

(51) Int. Cl.
*C07D 471/08* (2006.01)
*A61K 31/439* (2006.01)
*A61K 45/06* (2006.01)

(52) U.S. Cl.
CPC ............ *C07D 471/08* (2013.01); *A61K 45/06* (2013.01)

(58) Field of Classification Search
CPC ...... C07D 471/08; A61K 31/439; A61P 31/04
USPC .......................................... 546/121; 514/300
See application file for complete search history.

(56) References Cited

U.S. PATENT DOCUMENTS

| | | |
|---|---|---|
| 7,439,253 B2 | 10/2008 | Lampilas et al. |
| 8,487,093 B2 | 7/2013 | Blizzard |
| 10,800,778 B2 | 10/2020 | Comita-Prevoir |
| 11,814,385 B2 * | 11/2023 | Chen ................. C07D 471/08 |
| 2020/0165251 A1 | 5/2020 | Comita-Prevoir et al. |

FOREIGN PATENT DOCUMENTS

| | | |
|---|---|---|
| WO | 2002010172 | 2/2002 |
| WO | 2009091856 | 7/2009 |

OTHER PUBLICATIONS

Control, C. f. D. & Prevention. Antibiotic resistance threats in the United States, 2019. (US Department of Health and Human Services, Centres for Disease Control and . . . , 2019).
Paredes-Sabja, D., Shen, A. & Sorg, J. A. Clostridium difficile spore biology: sporulation, germination, and spore structural proteins. Trends in microbiology 22, 406-416 (2014).
Dembek, M. et al. High-throughput analysis of gene essentiality and sporulation in Clostridium difficile. MBio 6 (2015).

* cited by examiner

*Primary Examiner* — Charanjit Aulakh
(74) *Attorney, Agent, or Firm* — Meunier Carlin & Curfman LLC

(57) ABSTRACT

Disclosed herein are compounds that can prevent and treat *C. difficile* by inhibiting sporulation. Also disclosed herein are compositions and formulations comprising the compound disclosed herein. Methods of preventing and treating *C. difficile* comprising administering the compounds described herein are also disclosed.

16 Claims, 3 Drawing Sheets

| CD_2020 gene | B. subtilis 168 ortholog | Alternative designation | Category | MW (Da) | Essential? | Essential for sporulation? |
|---|---|---|---|---|---|---|
| 712 | PbpF or PbpG | PBP1 | HMM D,D transpeptidase, glycosyltransferase | 96570 | Yes | No |
| 1067 | SpoVD | PBP3 | HMM D,D transpeptidase | 62618 | No | Yes |
| 985 | PbpC | PBP2 | HMM D,D transpeptidase | 111412 | Yes | No |
| 2544 | SpoVD | SpoVD | HMM D,D transpeptidase | 73271 | No | Yes |
| 1131 | dacF | | D,D carboxypeptidase | 41992 | No | Yes |
| 1318 | | | - | 111800 | No | No |
| 2048 | dacF | | D,D carboxypeptidase | 44441 | No | Yes |
| 441 | | | D,D carboxypeptidase | 46078 | No | No |
| 3056 | amiE, formerly YbbE or pbpE | | AmpC-like β-lactamase | 38788 | No | Yes |
| 473 | | | 52809.41 | 52809.41 | No | No |
| VanG/1525 | | | D,D carboxypeptidase | | No | No |
| 2390 | | | D,D carboxypeptidase | 48236 | No | No |
| 2797 | | Ldt1 | L,D transpeptidase | 52520 | No | No |
| 2601 | | Ldt2 | L,D transpeptidase | 70993 | No | No |
| 2843 | | Ldt3 | L,D transpeptidase | 33366 | No | No |

FIG. 1

| Inhibitor | SpoVD IC50 (µM) | Sporulation inhibition (%) | Concentration (µg/mL) |
|---|---|---|---|
| Ceftazidime | 2.47 | 15.24 | 128 |
| Cefotaxime | 7.83 | 60.36 | 128 |
| Cefalothin | 0.27 | 76.67 | 32 |
| Cefoxitin | 0.94 | 98.51 | 32 |
| Ampicillin | 2.54 | 96.31 | 1 |
| Avibactam | 164.70 | 79.88 | 128 |
| Cloxacillin | 6.12 | 56.37 | 8 |
| Aztreonam | 1.36 | 69.35 | 128 |
| Ceftobiprole | 62.47 | 80.18 | 2 |
| Spo6 | 103.50 | 97.32 | 128 |
| Spo7 | 53.05 | 90.48 | 128 |
| Spo8 | 63.75 | 94.70 | 128 |

FIG. 2

SMALL MOLECULE INHIBITORS TARGETING *CLOSTRIDIOIDES DIFFICILE* SPORULATION

CROSS-REFERENCE TO RELATED APPLICATIONS

This application is a continuation of U.S. application Ser. No. 17/850,650, filed on Jun. 27, 2022, which claims the benefit of priority to U.S. Patent Application No. 63/202,834 filed on Jun. 25, 2021, the disclosure of which is expressly incorporated by reference herein in its entirety.

STATEMENT OF GOVERNMENT SUPPORT

This invention was made with government support under Grant No. R21 AI147654, awarded by the National Institutes of Health. The government has certain rights in the invention.

BACKGROUND

According to the CDC an estimated 500,000 *C. difficile* infections occur in the United States per year, making it the most common health-care associated infection. (Control, C. f. D. & Prevention.) Present treatments for CDI consist of oral metronidazole, vancomycin, and fidaxomicin, which is only partly effective as ~1 in 6 patients will relapse within two month.

The recurrence and spread of CDI is attributed to the spore, which is a robust, metabolically inert form of the bacterium that can withstand various environmental stressors and persist on surfaces for months. The spore is the primary vector for transmission and reinfection. (Paredes-Sabja et al.) There is a need for effective therapeutics that can kill *C. difficile* and/or prevent formation of the spore. There are no drugs that prevent sporulation.

The spore-cortex is a unique layer of peptidoglycan that is assembled through the action of D,D peptidase enzymes known as penicillin-binding proteins (PBPs). These PBPs are classified as either transpeptidases (TPases), which cross-link peptidoglycan, endopeptidases, and carboxypeptidases (CPases), which hydrolytically shorten the peptidoglycan stem and regulate the degree of cross-linking. Previous studies have found that deleting any of the TPase genes: CDR20291_2544 and CDR20291_1067 or the Cpase genes CDR20291_3056, CDR20291_2048, and CDR20291_1131 disrupts sporulation (FIG. 1). (Dembek et al.) It has previously been shown that β-lactam antibiotics, which bind strongly and irreversibly to PBPs, have potent anti-sporulation properties (FIG. 1, FIG. 2). However, the use of β-lactams for this purpose is not practical as they are causative agents of CDI.

In the mid-1990s a novel diazabicyclooctane (DBO) scaffold was discovered that inhibits serine β-lactamases. This scaffold was developed into avibactam, an FDA-approved drug. Because serine β-lactamases are evolutionary descendants of PBPs, the structural arrangement of the active site and catalytic motifs are highly conserved. However, while DBOs possess the covalent machinery to react with PBPs, they are relatively weak inhibitors against most TPases, and are non-bactericidal. Yet, this characteristic makes DBO compounds uniquely suited for targeting PBPs involved in sporogenesis, as it will not disrupt the gut microbiome and can withstand degradation from β-lactamases secreted by enteric bacteria.

SUMMARY

The present disclosure relates to compositions, preparations, and uses of therapeutic agents against bacterial infection. In one aspect, the present disclosure relates to bridged heterocyclic compounds that react with penicillin-binding proteins, alone and/or in combination with another antimicrobial agent to inhibit sporulation *C. difficile.*

Also disclosed are compounds with the structures of Formula Ia or Formula Ib:

Formula Ia

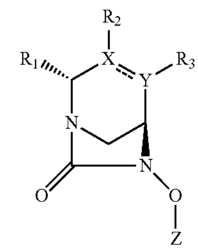

Formula Ib 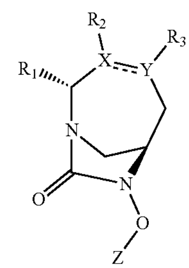 wherein $R_1$ is a monosubstituted amide bearing an unsubstituted or substituted aryl;

$R_2$ is hydrogen, —OH, halogen, unsubstituted or substituted $C_1$-$C_5$ alkyl, unsubstituted or substituted $C_1$-$C_5$ heteroalkyl, unsubstituted or substituted $C_2$-$C_5$ alkenyl, or unsubstituted or substituted $C_2$-$C_5$ heteroalkenyl;

$R_3$ is hydrogen, —OH, halogen, unsubstituted or substituted $C_1$-$C_5$ alkyl, unsubstituted or substituted $C_1$-$C_5$ heteroalkyl, unsubstituted or substituted $C_2$-$C_5$ alkenyl, or unsubstituted or substituted $C_2$-$C_5$ heteroalkenyl; or $R_2$ and $R_3$ together form a fused 4-8 membered ring and the fused ring is a substituted or unsubstituted aryl, substituted or unsubstituted heteroaryl, substituted or unsubstituted carbocycle, or a substituted or unsubstituted heterocycle;

X is saturated CH or unsaturated C;

Y is saturated CH or unsaturated C; and

Z is $SO_3H$, $PO_4H_2$, $CFHCO_2H$, or $CF_2CO_2H$.

Also disclosed herein is a pharmaceutical composition, comprising the compound disclosed herein and a pharmaceutically acceptable excipient.

Also disclosed herein is a method of prevent and treating *C. difficile*, comprising administering a therapeutically effective amount of the compound disclosed herein to a patient in need thereof.

The compounds disclosed herein can include heterocyclic compounds that prevent the sporulation process of *C. difficile* by inhibiting penicillin-binding proteins.

The present disclosure also provides pharmaceutical compositions of embodied compounds where they are used with an antibiotic to treat *C. difficile* infection by killing the bacterium and preventing sporulation.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The accompanying figures, which are incorporated in and constitute a part of this specification, illustrate several aspects of the disclosure, and together with the description, serve to explain the principles of the disclosure.

FIG. 1 is a table of *C. difficile* PBPs and their essentialities for vegetative growth and sporulation.

FIG. 2 is a table of $IC_{50}$ values of select $-lactam antibiotics against SpoVD, their percentage inhibition of sporulation, and the concentration at which they were tested (½ MIC).

FIG. 3A shows the data for ampicillin, FIG. 3B shows the data for meropenem, and FIG. 3C shows the data for cefoxitin.

FIG. 4A shows avibactam, FIG. 4B shows Spo6, FIG. 4C shows Spo7, FIG. 4D sows Spo8, FIG. 4E shows Spo9, and FIG. 4F shows Spo10.

FIG. 6A shows the crystal structure of PBP3 in complex with Spo6. FIG. 6B shows the chemical structure of avibactam, FIG. 6B shows the chemical structure of Spo6, FIG. 6C shows the chemical structure of Spo9, FIG. 6D shows the chemical structure of Spo11, and FIG. 6E shows the chemical structure of Spo11, and FIG. 6F shows the chemical structure of Spo12.

DETAILED DESCRIPTION

Figures 3A, 3B, 3C:
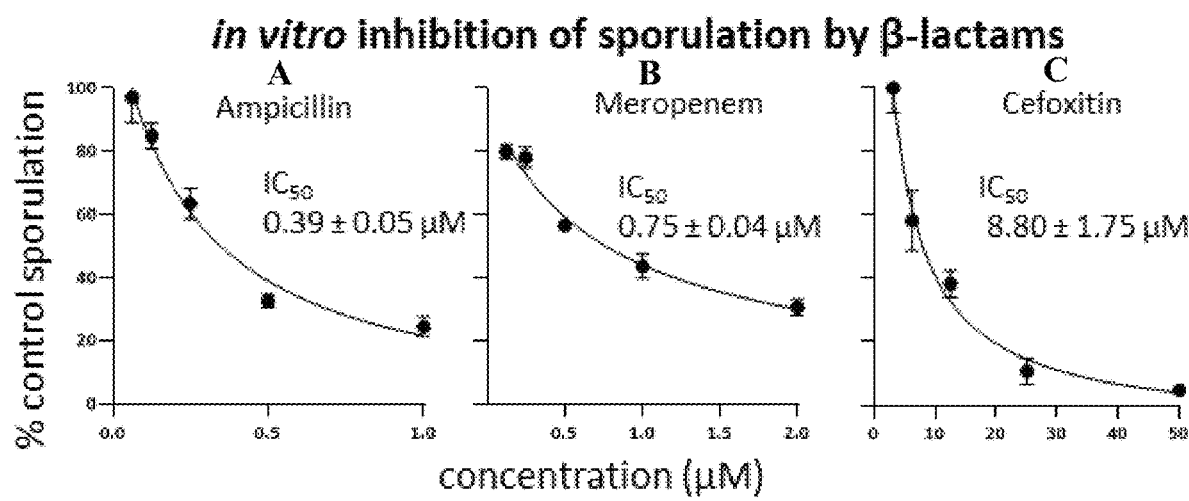
FIGS. 3A-3C show graphs of in vitro inhibition of sporulation by β-lactam belonging to the three main classes of β-lactams: the penicillins, the carbapenems, and the cephalosporins.
Figures 4A, 4B, 4C, 4D, 4E, 4F:
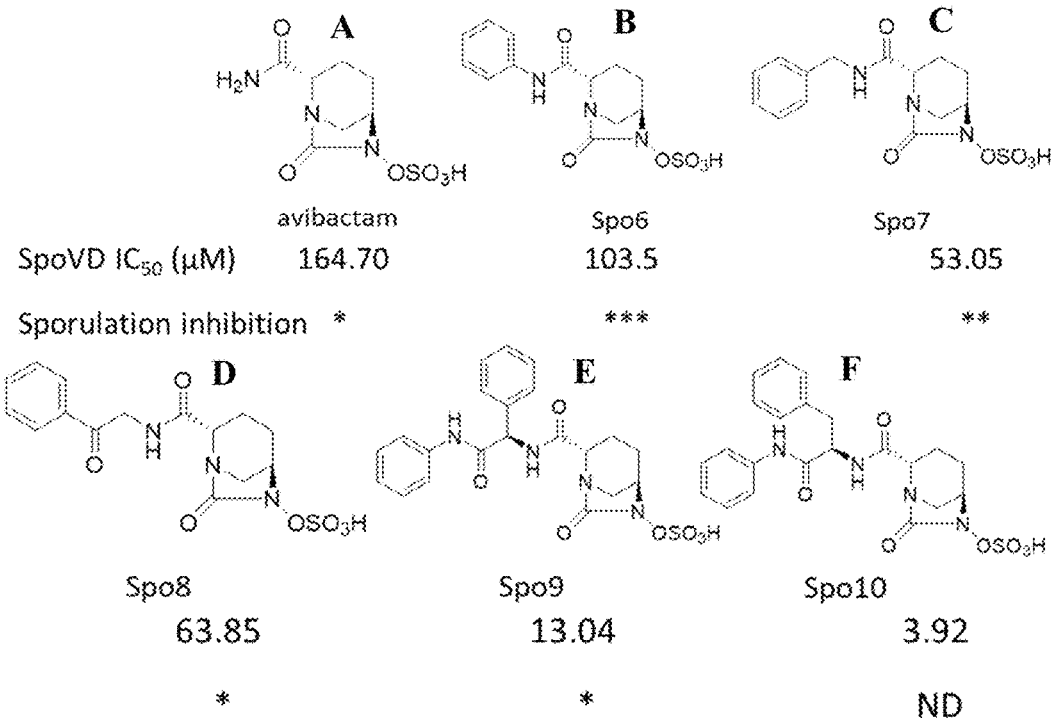
FIGS. 4A-4F show chemical structures of DPO sporulation inhibitors, their biochemical inhibition against SpoVD and their in vitro sporulation inhibition, wherein * indicates >50%,  indicates >90%, and *>95%.
Figures 5A, 5B:
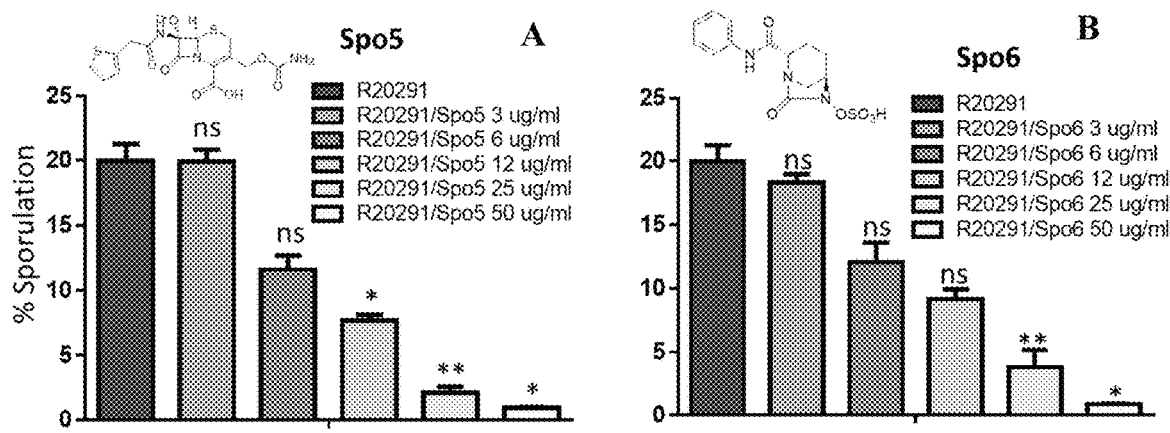
FIGS. 5A-5B are graphs of dose dependent sporulation inhibition of cefoxitin (FIG. 5A) vs. Spo6 (FIG. 5B).
Figures 6A, 6B, 6C, 6D, 6E, 6F:
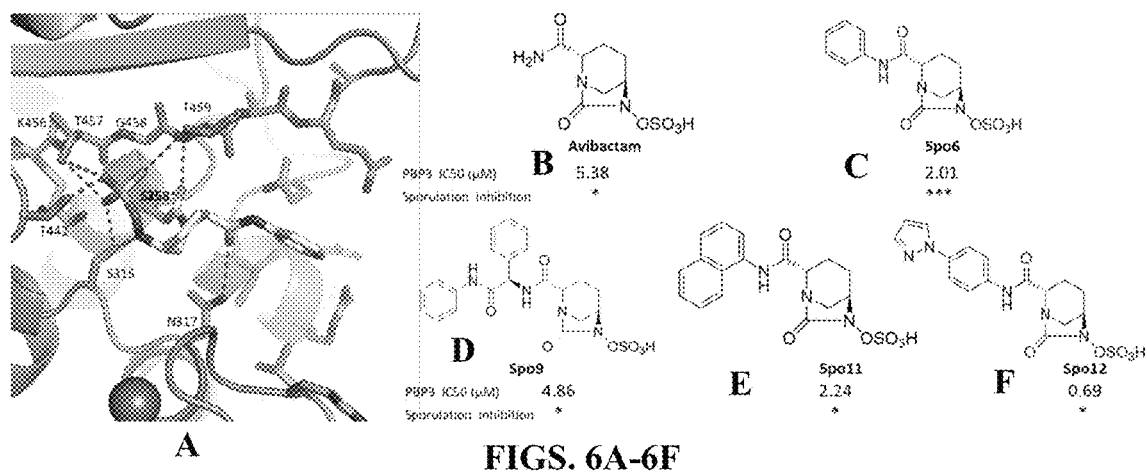
FIGS. 6A-6F show the crystal structure of PBP3 and the chemical structures of DBO sporulation inhibitors, wherein * indicates >50%,  indicates >90%, and *>95%.

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

In this specification and in the claims that follow, reference will be made to a number of terms, which shall be defined to have the following meanings.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of,"

"including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint.

The term "patient" refers to a human in need of treatment for any purpose. However, the term "patient" can also refer to non-human animals, preferably mammals such as dogs, cats, horses, cows, pigs, sheep and non-human primates, among others, that are in need of treatment.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

A residue of a chemical species, as used herein, refers to a derivative of a moiety that is present in a particular product. To form the product, at least one atom of the moiety is replaced by a bond to a second moiety, such that the product contains a derivative of a moiety. For example, in some embodiments, an aromatic residue in a product may refer to one or more —$(C_6H_5)_n$ units present in a cyclic peptide described herein. Similarly, an amino acid residue in a product may refer to cyclic peptide described herein having an amino acid incorporated therein through formation of one or more peptide bonds, and such residues may be referred to interchangeably herein as an amino acid or an amino acid residue.

As used herein "aromatic" refers to an unsaturated cyclic molecule having $4n+2\pi$ electrons, wherein n is any integer. The term "non-aromatic" refers to any unsaturated cyclic molecule which does not fall within the definition of aromatic.

"Alkyl" or "alkyl group" refers to a fully saturated, straight or branched hydrocarbon chain radical having from one to forty carbon atoms, and which is attached to the rest of the molecule by a single bond. Alkyls comprising any number of carbon atoms from 1 to 20 are included. An alkyl comprising up to 40 carbon atoms is a $C_1$-$C_{40}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted.

"Alkenyl" or "alkenyl group" refers to a straight or branched hydrocarbon chain radical having from two to forty carbon atoms, and having one or more carbon-carbon double bonds. Each alkenyl group is attached to the rest of the molecule by a single bond. Alkenyl group comprising any number of carbon atoms from 2 to 40 are included. An alkenyl group comprising up to 40 carbon atoms is a $C_2$-$C_{40}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkoxy" refers to the group —OR, where R is alkyl, alkenyl, alkynyl, cycloalkyl, or heterocyclyl as defined herein. Unless stated otherwise specifically in the specification, alkoxy can be optionally substituted.

"Alkylthio" refers to the —SR or —S(O)$_{n=1-2}$—R, where R is alkyl, alkenyl, alkynyl, cycloalkyl, cycloalkenyl, cycloalkynyl, or hetereocyclyl, as defined herein. Unless stated otherwise specifically in the specification, alkylthio can be optionally substituted.

"Alkynyl" or "alkynyl group" refers to a straight or branched hydrocarbon chain radical having from two to forty carbon atoms, and having one or more carbon-carbon triple bonds. Each alkynyl group is attached to the rest of the molecule by a single bond. Alkynyl group comprising any number of carbon atoms from 2 to 40 are included. An alkynyl group comprising up to 40 carbon atoms is a $C_2$-$C_{40}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable 3- to 20-membered non-aromatic ring radical, which consists of two to fourteen carbon atoms and from one to eight heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl is monovalent and is attached to the rest of molecule through a single bond. In some embodiments, the heterocyclyl is divalent and is independently attached to two moieties through single bonds. Unless stated otherwise specifically in the specification, a heterocyclyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized.

Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

The term "substituted" used herein means any of the above groups (i.e., alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio) wherein at least one atom is replaced by a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more atoms are replaced by an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. "Substituted" can also mean an amino acid in which one or more atoms on the side chain are replaced by alkyl, alkenyl, alkynyl, acyl, alkylcarboxamidyl, alkoxycarbonyl, carbocyclyl, heterocyclyl, aryl, or heteroaryl. In addition, each of the foregoing substituents can also be optionally substituted with one or more of the above substituents.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture. Unless stated to the contrary, a formula depicting one or more stereochemical features does not exclude the presence of other isomers.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Compounds

Disclosed herein are compounds of Formula Ia or Formula Ib:

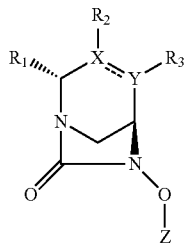

Formula Ia

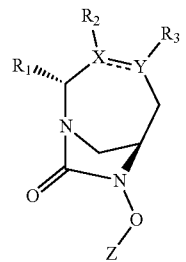

Formula Ib or pharmaceutically acceptable salts thereof. In some examples, the compound has Formula Ia, wherein:

$R_1$ is a monosubstituted amide bearing an unsubstituted or substituted aryl, unsubstituted or substituted alkyl, or unsubstituted or substituted heteroaryl;

$R_2$ is hydrogen, —OH, halogen, unsubstituted or substituted $C_1$-$C_5$ alkyl, unsubstituted or substituted $C_1$-$C_5$ heteroalkyl, unsubstituted or substituted $C_2$-$C_5$ alkenyl, or unsubstituted or substituted $C_2$-$C_5$ heteroalkenyl;

$R_3$ is hydrogen, —OH, halogen, unsubstituted or substituted $C_1$-$C_5$ alkyl, unsubstituted or substituted $C_1$-$C_5$ heteroalkyl, unsubstituted or substituted $C_2$-$C_5$ alkenyl, or unsubstituted or substituted $C_2$-$C_5$ heteroalkenyl; or R₂ and R₃ together form a fused 4-8 membered ring and the fused ring is a substituted or unsubstituted aryl, substituted or unsubstituted heteroaryl, substituted or unsubstituted carbocycle, or a substituted or unsubstituted heterocycle;

X is saturated CH or unsaturated C;

Y is saturated CH or unsaturated C; and

Z is $SO_3H$, $PO_4H_2$, $CFHCO_2H$, or $CF_2CO_2H$.

In further examples, $R_2$ and $R_3$ are the same. In certain examples, $R_2$ and $R_3$ are hydrogen.

In specific examples, X and Y are the same. In some examples, X and Y are unsaturated CH.

In further examples, Z is $SO_3H$.

In certain examples, $R_1$ is a monosubstituted amide bearing an unsubstituted $C_1$-$C_6$ alkyl. In certain examples, $R_1$ is a monosubstituted amide bearing an unsubstituted aryl or a substituted aryl. In specific examples, $R_1$ is a monosubstituted amide bearing an unsubstituted aryl. In some examples, the unsubstituted aryl is phenyl. In further examples, $R_1$ is a monosubstituted amide bearing a substituted phenyl. In certain examples, the substituted phenyl is substituted at any position with a halogen, hydroxyl, alkyl, $C_3$-$C_8$ cycloalkyl, aryl, or $C_2$-$C_8$ heteroaryl. In some examples, the substituted phenyl is substituted at any position with urea, an amine, or an alkylamine. In specific examples, $R_1$ is $Ph(CH_2)_{0-2}$—NHC(O)—.

In certain examples, the compound is Spo6:

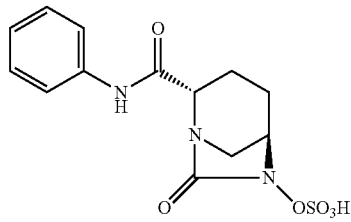

Spo6

In further examples, the unsubstituted aryl is benzyl. In specific examples, the compound is Spo7:

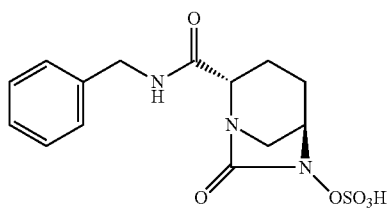

Spo7

In some examples, $R_1$ is a monosubstituted amide with the following formula:

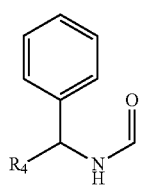

Formula II wherein $R_4$ is an unsubstituted or substituted amide. In further examples, $R_4$ is a monosubstituted amide. In certain examples, $R_4$ is a monosubstituted amide bearing an unsubstituted aryl or substituted aryl. In specific examples, $R_4$ is a monosubstituted amide bearing an unsubstituted aryl. In some examples, $R_4$ is a monosubstituted amide bearing a phenyl. In further examples, $R_4$ has Formula III:

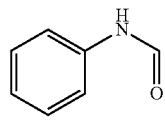

Formula III

In certain examples, $R_1$ has Formula IV:

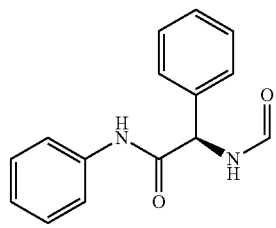

Formula IV

In certain examples, the compounds is Spo9:

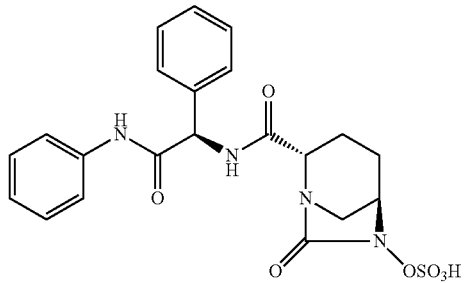

Spo9

In some examples, $R_1$ is a monosubstituted amide bearing an unsubstituted polycyclic aryl. In further examples, the unsubstituted polycyclic aryl is a benzenoid polycyclic aryl. In certain examples, the benzenoid polycyclic aryl is naphthalene. In specific examples, the compound is Spo11:

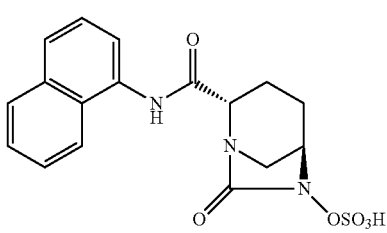

Spo11

In some examples, $R_1$ is a monosubstituted amide bearing a substituted aryl. In further examples, the substituted aryl is a para-substituted aryl. In certain examples, the para-substituted aryl is substituted with a heteroaryl. In specific examples, the heteroaryl comprises at least one nitrogen. In further examples, the heteroaryl is a pyrazole. In certain examples, the compound is Spo12:

Spo12

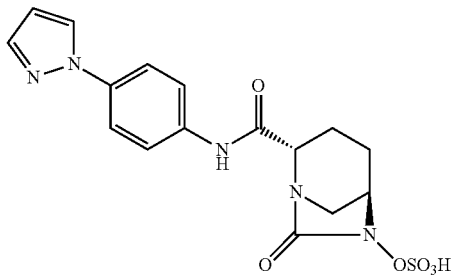

In specific examples, $R_1$ is a monosubstituted amide bearing an alkyl aryl ketone. In some examples, the aryl in the alkyl aryl ketone is substituted. In further examples, the aryl in the alkyl aryl ketone is unsubstituted. In certain examples, $R_1$ has Formula V:

Formula V

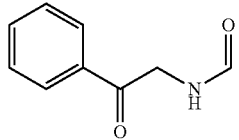

In specific examples, the compound is Spo8:

Spo8

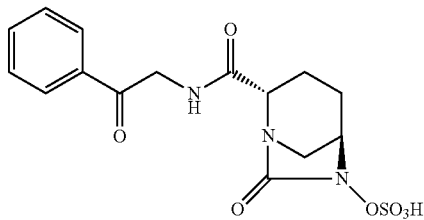

In some examples, $R_1$ is a monosubstituted amide bearing ethyl benzene. In further examples, $R_1$ is a monosubstituted amide with the following formula:

Formula VI

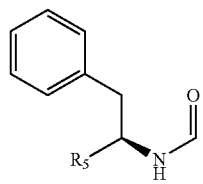

In certain examples, $R_5$ is an unsubstituted amide or a monosubstituted amide. In specific examples, the monosubstituted amide bears an unsubstituted aryl or substituted aryl. In some examples, the unsubstituted aryl is a phenyl. In further examples, $R_5$ has the following formula:

Formula VII

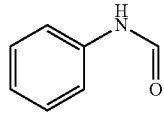

In certain examples, $R_1$ has Formula VIII:

Formula VIII

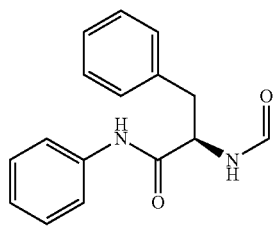

In specific examples, the compound is Spo10:

Spo10

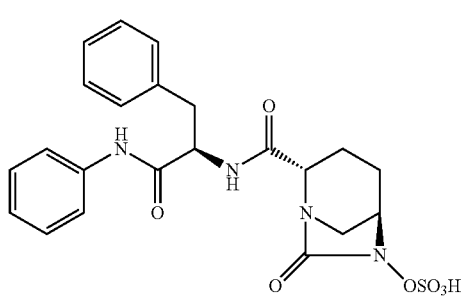

In some examples, $R_1$ is a di-substituted amide. In further examples, the di-substituted amide is substituted with a halogen, hydroxyl, alkyl, cycloalkyl, aryl, heteroaryl, or any combination thereof. In certain examples, the compound has Formula IX:

Formula IX

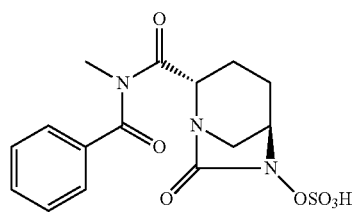

In specific examples, the compound has Formula X:

Formula X

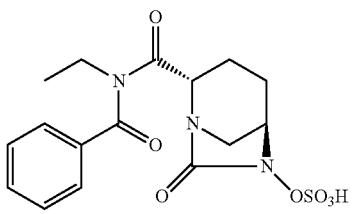

Compositions, Formulations, Methods of Treating and Preventing *C. Difficile*, and Methods of Administration Further presented herein is a pharmaceutical composition comprising the compound disclosed herein alone or in combination with an antibiotic.

The compounds described herein can be administered adjunctively with other active compounds. These additional active compounds include but are not limited to antibiotics, analgesics, anti-inflammatory drugs, antihistamines, sedatives, corticosteroids, electrolytes, gastro-intestinal drugs, muscle relaxants, nutritional agents, vitamins, parasympathomimetics, stimulants, and antiviral agents. "Adjunctive administration", as used herein, means the compound can be administered in the same dosage form or in separate dosage forms with one or more other active agents. The additional active agent(s) can be formulated for immediate release, controlled release, or combinations thereof. In some examples, antibiotics can include antibiotics used to prevent or treat *C. difficile*, which can include, but are not limited to, vancomycin, fidaxomicin, or any combination thereof.

Further presented herein is a formulation comprising the compound disclosed herein and a pharmaceutically acceptable excipient.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Stabilizers are used to inhibit or retard drug decomposition reactions which include, by way of example, oxidative reactions.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Further presented herein is a method of preventing and treating *C. difficile*, comprising administering a therapeutically effective amount of the compound disclosed herein to a patient in need thereof. In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The disclosed compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

The dose administered to a patient, particularly a human, should be sufficient to achieve a therapeutic response in the patient over a reasonable time frame, without lethal toxicity, and preferably causing no more than an acceptable level of side effects or morbidity.

One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: General Procedures

Bacillin Inhibition Assay

Reactions were performed in a 96-well polystyrene plate with a final volume of 60 µl at 37° C. in 1× tris-buffered saline (20 mM Tris, 150 mM NaCl). For IC50 values, inhibitor were serially diluted with a 2-fold scheme so the highest concentration had a final value of 1 mM or 500 µM and the final concentration was either 0.97 or 0.489 µM. Protein was then diluted and added to the well for a final concentration of 1 µM and incubated for 15 minutes at 37° C. 1 µL of bocillin (BOCILLIN™ FL Penicillin, Sodium Salt, Thermo Fisher Scientific) was added to each well for a final concentration of 20 µM, and incubated for 10 minutes at 37° C. Reactions were killed with 10 µL of 6×SDS loading buffer and pooled or directly loaded onto a 15-well Novex Wedgewell 8% Tris-Glycine Gels and ran at 175 V for ~1 hour. Gels were then imaged (Biorad) for 6 seconds with the fluorescein blot filter setting and analyzed using ImageJ. All values were normalized to background intensity and divided by the average of three control intensities (no inhibitor) for % inhibition value. Assays were performed in duplicate or triplicate and IC50 values were calculated using a 3-parameter nonlinear regression.

Nitrocefin Inhibition Assay

Reactions were performed in a 96-well polystyrene plate with a final volume of 60 µl at 37° C. in 20 mM Tris pH 8.5, 200 mM NaCl. Inhibitors were diluted for a final concentration of 25 µM. Protein was then added to the well for a final concentration of 1 µM and incubated for 15 minutes at 37° C. 1 µL of nitrocefin was then added to each well for a final concentration of 20 µM, and reaction progress was monitored using a Biotek Cytation 5 plate reader at 488 nM and 37° C. for 1 hour. Reaction rates were normalized to the control (no inhibitor) for % inhibition values. Assays were performed in duplicate or triplicate and IC50 values were calculated using a 3-parameter nonlinear regression.

Protein Purification

The coding sequence corresponding to the soluble constructs of CDR20291_1067 (PBP3), CDR20291_0985 (PBP2) and CDR20291_2544 (CdSpoVD) were amplified from C. difficile R20291 genomic DNA The expression vector was modified from pETGST, in which the thrombin cleavage site was replaced by TEV (named pETGSTTEV) or ULP1 (named pETGSTSUMO) cleavage site. The vector was digested and the PCR fragments for each protein was inserted into the multi-clone site accordingly. SpovD 38-583 inserted into the NheI/XhoI site of the pETGSTSUMO vector. Cloned vector was then transformed into BL21(DE3) pLysS Escherichia coli (E. coli). Standard overnight cultures were grown in LB media containing chloramphenicol and kanamycin and used to inoculate 1 L LB cultures.

Cultures were grown until the optical density (OD600) reached ~0.7. Protein expression was then induced with 0.5 mM isopropyl-β-d-thiogalactopyranoside (IPTG) overnight at 20° C. Cells were harvested via centrifugation at 4000×g for 10 minutes at 4° C. The cell pellet was suspended with a solution of 20 mM Tris pH 8.0, 200 mM NaCl, 20 mM imidazole, and one dissolved Thermo Scientific™ Pierce Protease Inhibitor Tablets. Cells were lysed with a sonicator using a 10 second sonication/15 second rest cycle for 15 minutes. Cell lysate was centrifuged at 45,000×g for 35 minutes and supernatant was loaded onto a HisTrap affinity column (GE Healthcare). A linear gradient of buffer B (20 mM Tris pH 8.0, 300 mM NaCl, 500 mM imidazole, and 10% glycerol) was applied to elute the recombinant protein which usually occurred at 30% buffer B. These fractions were pooled and buffer exchanged three times into protease buffer (20 mM Tris pH 8.0, 10% glycerol) using an Amicon Ultra centrifugal filter (Sigma-Aldrich). Purified His6-tagged TEV protease was added to all proteins at a 1:20 ratio except for CdSpoVD and incubated overnight at 4° C. Pure His6-tagged ULP1 protease was added to CdSpoVD at 1:20 ratio and incubated overnight at 4° C. The digested protein was re-loaded onto the HisTrap affinity column. Flow-through was collected, concentrated, and loaded to a HiLoad 16/60 Superdex 75 size exclusion column (GE Healthcare) where it ran at a flow rate of 0.5 ml/min. Peak fractions were combined and purity assessed (>95%) with gel-electrophoresis. The identity of each enzyme was independently characterized with gel-electrophoresis, native-mass spectrometry, bocillin or nitrocefin binding, and/or X-ray crystallography.

Example 2: Synthesis

General Procedure A: Coupling Reaction 4.001 (0.240 g, 0.869 mmol) was dissolved in DCM (32.2 mL) to provide a clear solution. Benzylamine (0.142 mL, 1.30 mmol), HOAt (1.30 mL, 1.30 mmol), and EDC (0.250 g, 1.30 mmol) were added to the solution which resulted in a yellow suspension. The mixture was allowed to stir overnight. The mixture was then washed with brine, dried over MgSO$_4$, and concentrated under reduced pressure to afford a yellow oil. The crude product was purified by flash chromatography on silica gel (100:0-1:1 hexanes:ethyl acetate) to give compound 4.002 (0.302 g, 94%) as a white solid. $^1$H NMR (CHLOROFORM-d, 400 MHz) δ 7.4-7.4 (m, 2H), 7.2-7.4 (m, 8H), 5.0-5.1 (m, 1H), 4.88 (d, 1H, J=11.4 Hz), 4.4-4.5 (m, 2H), 3.93 (br d, 1H, J=7.4 Hz), 3.26 (br s, 1H), 2.9-3.0 (m, 2H), 2.65 (d, 1H, J=11.5 Hz), 2.40 (br dd, 1H, J=6.5, 14.4 Hz), 1.9-2.0 (m, 2H), 1.6-1.6 (m, 1H) ppm. $^{13}$C NMR (CHLOROFORM-d, 151 MHz) δ 169.5, 167.6, 137.9, 135.7, 129.3, 128.8, 128.8, 128.6, 127.8, 127.6, 78.3, 60.6, 57.9, 47.7, 43.7, 20.9, 17.4 ppm.

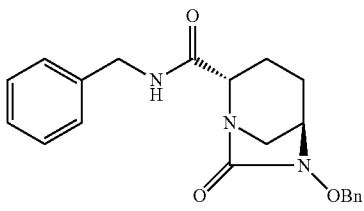

4.002

General Procedure B: Deprotecting and Sulfating

Compound 4.002 (0.078 g, 0.213 mmol) was dissolved in isopropyl alcohol (5.08 mL) under argon in a reaction vial. Palladium on carbon (0.0510 g, 0.0480 mmol) and ammonium formate (0.020 g, 0.320 mmol) were added to the solution and stirred until completion at room temperature. The reaction was monitored by TLC for loss of starting material. The reaction was filtered over celite and the filtrate was concentrated under reduced pressure resulting in a yellow oil. The oil was dissolved in isopropyl alcohol (5.08 mL). Triethylamine (0.00593 mL, 0.0430 mmol) and sulfur trioxide trimethylamine complex (0.0330 g, 0.239 mmol) were added to the solution. The resulting suspension was stirred until completion. The solvent was concentrated under reduced pressure and water was added. The aqueous layer was washed with DCM. The aqueous layer was concentrated under reduced pressure to give a yellow oil. The crude product was further purified by reverse phase preparative HPLC a give compound 4.009 (0.0700 g, 92%) as a white solid. $^{1}$H NMR (DEUTERIUM OXIDE, 400 MHz) δ 7.2-7.3 (m, 3H), 7.22 (br d, 4H, J=7.3 Hz), 4.3-4.4 (m, 3H), 4.04 (br s, 1H), 3.94 (br d, 1H, J=7.5 Hz), 3.17 (br d, 1H, J=12.0 Hz), 2.9-2.9 (m, 1H), 2.0-2.1 (m, 1H), 1.9-2.0 (m, 1H), 1.7-1.9 (m, 1H), 1.6-1.7 (m, 1H) ppm. $^{13}$C NMR (DEUTERIUM OXIDE, 151 MHz) δ 171.9, 138.0, 128.8, 127.4, 127.3, 60.5, 59.8, 47.0, 43.2, 19.8, 18.1 ppm. HRMS m/z: [M-H]$^{-}$ calcd for $C_{14}H_{17}N_{3}O_{6}S$ 355.0837; found 354.0764.

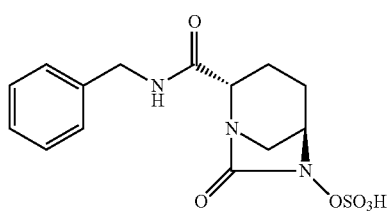

4.009

Synthesis Procedure

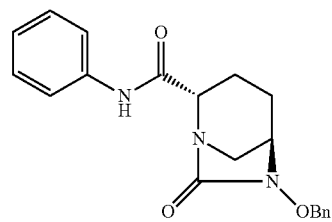

4.003

Using general procedure A 4.001 and aniline were converted to 4.003 (78%) to give a clear oil. $^{1}$H NMR (CHLOROFORM-d, 400 MHz) δ 7.51 (d, 2H, J=7.8 Hz), 7.3-7.4 (m, 7H), 7.1-7.1 (m, 1H), 5.0-5.1 (m, 1H), 4.90 (d, 1H, J=11.4 Hz), 4.04 (br d, 1H, J=7.2 Hz), 3.32 (br s, 1H), 3.0-3.1 (m, 1H), 2.74 (d, 1H, J=11.6 Hz), 2.4-2.5 (m, 1H), 1.9-2.1 (m, 2H), 1.6-1.7 (m, 1H) ppm. $^{13}$C NMR (CHLOROFORM-d, 101 MHz) δ 167.6, 167.3, 137.4, 135.5, 129.2, 129.0, 128.8, 128.6, 124.4, 119.4, 78.3, 61.0, 57.7, 47.7, 20.7, 17.1 ppm.

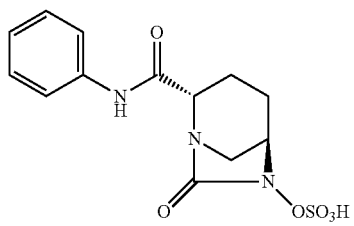

4.010

Using general procedure B compound 4.003 was converted to 4.010 (84%) to give a white solid. $^{1}$H NMR (DEUTERIUM OXIDE, 400 MHz) δ 7.3-7.4 (m, 4H), 7.1-7.2 (m, 1H), 4.1-4.1 (m, 2H), 3.2-3.3 (m, 1H), 2.1-2.2 (m, 1H), 1.9-2.0 (m, 1H), 1.8-1.9 (m, 1H), 1.7-1.8 (m, 1H) ppm. $^{13}$C NMR (DEUTERIUM OXIDE, 151 MHz) δ 170.5, 169.3, 136.3, 129.2, 126.0, 122.4, 60.8, 59.8, 47.0, 46.7, 19.8, 18.0 ppm. HRMS m/z: [M-H]$^{-}$ calcd for $C_{13}H_{15}N_{3}O_{6}S$ 341.0681; found 340.0609.

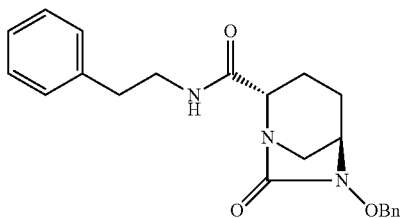

4.004

Using general procedure A 4.001 and phenethylamine were converted to 4.004 (87%) to give a white solid. $^{1}$H NMR (CHLOROFORM-d, 400 MHz) δ 7.3-7.4 (m, 4H), 7.2-7.3 (m, 2H), 7.1-7.2 (m, 3H), 5.01 (d, 1H, J=11.5 Hz), 4.86 (d, 1H, J=11.5 Hz), 3.82 (d, 1H, J=7.5 Hz), 3.6-3.7 (m, 1H), 3.47 (qd, 1H, J=6.5, 12.9 Hz), 3.24 (br s, 1H), 2.7-2.9 (m, 3H), 2.3-2.4 (m, 1H), 1.8-2.0 (m, 2H), 1.5-1.6 (m, 1H) ppm. $^{13}$C NMR (CHLOROFORM-d, 101 MHz) δ 169.5, 167.7, 138.5, 135.6, 129.1, 128.6, 128.5, 126.5, 78.2, 60.5, 57.8, 47.4, 40.4, 35.6, 20.8, 17.3 ppm.

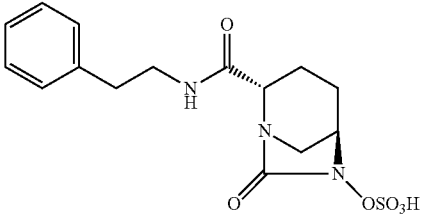

4.011

Using general procedure B, 4.004 was converted to 4.010 (80%) to give a white solid. $^{1}$H NMR (DEUTERIUM OXIDE, 600 MHz) δ 7.3-7.3 (m, 2H), 7.2-7.3 (m, 3H), 4.02

(br d, 1H, J=2.9 Hz), 3.83 (br d, 1H, J=7.6 Hz), 3.5-3.6 (m, 1H), 3.42 (td, 1H, J=6.6, 13.6 Hz), 3.02 (br d, 1H, J=12.4 Hz), 2.81 (qd, 2H, J=7.1, 17.6 Hz), 2.52 (d, 1H, J=12.0 Hz), 2.0-2.0 (m, 1H), 1.9-2.0 (m, 1H), 1.7-1.8 (m, 1H), 1.5-1.6 (m, 1H) ppm. $^{13}$C NMR (DEUTERIUM OXIDE, 151 MHz) δ 171.5, 169.4, 139.1, 129.0, 128.7, 126.6, 60.4, 59.7, 46.8, 40.3, 34.4, 19.8, 18.1 ppm. HRMS m/z: [M-H]$^-$ calcd for C$_{15}$H$_{19}$N$_3$O$_6$S 369.0992; found 368.0919.

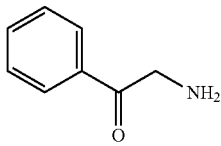

4.015

Compound 4.015 was synthesized using a known procedure from the literature. (azide)$^1$H NMR (CHLOROFORM-d, 600 MHz) δ 7.78 (br d, 2H, J=8.0 Hz), 7.5-7.5 (m, 1H), 7.4-7.4 (m, 2H), 4.44 (s, 2H) ppm. (amine)$^1$H NMR (METHANOL-d$_4$, 600 MHz) δ 8.0-8.1 (m, 1H), 7.7-7.8 (m, 2H), 7.6-7.6 (m, 1H), 7.6-7.6 (m, 1H), 7.2-7.3 (m, 1H), 4.61 (s, 1H), 2.4-2.4 (m, 2H) ppm.

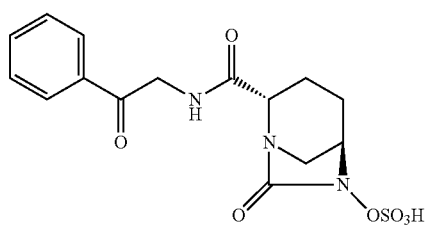

4.005

Using general procedure A, 4.001 2-amino-1-phenethanone were converted to 4.005 (86%) to give a tan solid. $^1$H NMR (CHLOROFORM-d, 600 MHz) δ 7.9-7.9 (m, 5H), 7.5-7.6 (m, 1H), 7.43 (t, 5H, J=7.8 Hz), 7.4-7.4 (m, 3H), 7.3-7.3 (m, 4H), 5.0-5.0 (m, 1H), 4.9-5.0 (m, 1H), 4.86 (d, 1H, J=11.3 Hz), 4.50 (dd, 1H, J=4.0, 19.3 Hz), 3.97 (d, 1H, J=7.6 Hz), 3.2-3.3 (m, 1H), 3.06 (br d, 1H, J=12.0 Hz), 2.89 (d, 1H, J=11.6 Hz), 2.3-2.4 (m, 1H), 1.9-2.0 (m, 2H) ppm. $^{13}$C NMR (CHLOROFORM-d, 151 MHz) δ 194.0, 170.2, 167.7, 135.7, 134.5, 134.1, 129.3, 128.9, 128.8, 128.6, 127.9, 78.3, 60.5, 57.9, 17.6 ppm.

4.012

Using general procedure B, 4.005 was converted to 4.012 (84%) to give an orange oil. $^1$H NMR (DEUTERIUM OXIDE, 600 MHz) δ 7.94 (d, 2H, J=8.0 Hz), 7.6-7.7 (m, 1H), 7.52 (s, 2H), 4.8-4.8 (m, 1H), 4.16 (br s, 1H), 4.09 (br d, 1H, J=7.6 Hz), 3.3-3.3 (m, 1H), 3.2-3.2 (m, 1H), 2.1-2.2 (m, 1H), 2.03 (br dd, 2H, J=3.6, 14.5 Hz), 1.9-1.9 (m, 1H), 1.7-1.8 (m, 2H) ppm. HRMS m/z: [M-H]$^-$ calcd for C$_{15}$H$_{17}$N$_3$O$_7$S 383.0792; found 382.0702.

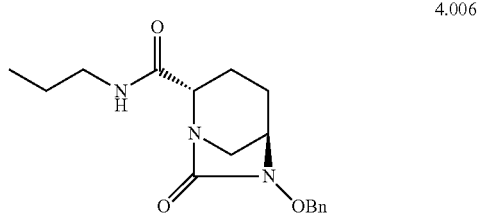 [SMILES: CCCNC(=O)[C@@H]1CC[C@@H]2CN1C(=O)N2OCc1ccccc1]

4.006

Using general procedure A, 4.001 propylamine were converted to 4.006 (76%) to give an off-white solid. $^1$H NMR (CHLOROFORM-d, 400 MHz) δ 7.3-7.4 (m, 2H), 7.3-7.3 (m, 3H), 6.6-6.7 (m, 1H), 4.9-5.0 (m, 1H), 4.8-4.8 (m, 1H), 3.80 (br d, 1H, J=7.6 Hz), 3.24 (br s, 1H), 3.15 (q, 2H, J=6.4 Hz), 2.9-2.9 (m, 1H), 2.63 (d, 1H, J=11.5 Hz), 2.3-2.3 (m, 1H), 1.8-1.9 (m, 2H), 1.5-1.6 (m, 1H), 1.4-1.5 (m, 2H), 0.82 (t, 3H, J=7.4 Hz) ppm. $^{13}$C NMR (CHLOROFORM-d, 101 MHz) δ 169.4, 167.7, 135.5, 129.1, 128.7, 128.5, 78.1, 60.4, 57.8, 47.5, 41.1, 22.7, 20.8, 17.4, 11.3 ppm.

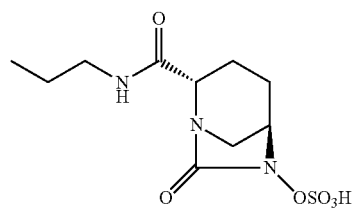

4.013

Using general procedure B 4.006 was converted to 4.014 (80%) to give a white solid. $^1$H NMR (DEUTERIUM OXIDE, 400 MHz) δ 4.1-4.1 (m, 1H), 3.88 (br d, 1H, J=7.3 Hz), 3.1-3.2 (m, 2H), 2.9-3.0 (m, 1H), 2.0-2.1 (m, 1H), 1.9-2.0 (m, 1H), 1.7-1.8 (m, 1H), 1.6-1.7 (m, 1H), 1.3-1.4 (m, 2H), 0.75 (t, 3H, J=7.4 Hz) ppm. $^{13}$C NMR (DEUTERIUM OXIDE, 151 MHz) δ 171.7, 169.5, 60.5, 59.8, 46.9, 41.3, 21.9, 19.9, 18.3, 10.7 ppm. [M-H]$^-$ calcd for C$_{10}$H$_{17}$N$_3$O$_6$S 307.0843; found 306.077.

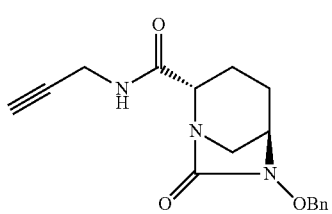

4.007

Using general procedure A, 4.001 and propargylamine were converted to 4.007 (90%) to give a white solid. $^1$H NMR (CHLOROFORM-d, 400 MHz) δ 7.3-7.4 (m, 5H), 5.02 (d, 1H, J=11.4 Hz), 4.9-4.9 (m, 1H), 4.1-4.1 (m, 1H), 4.1-4.1 (m, 1H), 4.0-4.0 (m, 1H), 3.9-4.0 (m, 1H), 3.88 (br d, 1H, J=7.3 Hz), 3.27 (br s, 1H), 2.99 (br d, 1H, J=11.6 Hz), 2.6-2.7 (m, 1H), 2.34 (br dd, 1H, J=6.4, 14.5 Hz), 2.18 (t, 1H, J=2.4 Hz), 1.9-2.0 (m, 2H), 1.5-1.6 (m, 1H) ppm. $^{13}$C NMR (CHLOROFORM-d, 101 MHz) δ 169.4, 167.4, 135.6, 129.2, 128.8, 128.5, 79.1, 78.2, 71.6, 60.4, 57.7, 47.5, 29.2, 20.7, 17.3 ppm.

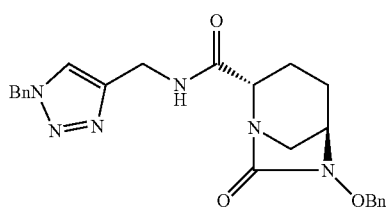

4.008

In a 5 mL round bottomed flask was amide 4.007 (0.0850 g, 0.271 mmol) and benzyl azide (0.0339 mL, 0.271 mmol) were dissolved in 1:1 water:butanol (0.675 water, 0.675 butanol). Sodium ascorbate (0.00475 g, 0.0270 mmol) and copper sulfate (0.00217 g, 0.0140 mmol) were added to the reaction. The reaction was stirred at room temperature until completion. The solvent was removed under reduced pressure The crude product was purified by flash chromatography on silica gel (100:0-1:1 hexanes:ethyl acetate) to give compound 4.008 (0.117 g, 97%) as a colorless oil. $^1$H NMR (CHLOROFORM-d, 400 MHz) δ 7.3-7.4 (m, 9H), 7.2-7.2 (m, 2H), 5.4-5.5 (m, 3H), 5.0-5.0 (m, 1H), 4.8-4.9 (m, 1H), 4.4-4.5 (m, 2H), 3.84 (br d, 1H, J=7.3 Hz), 3.2-3.2 (m, 1H), 2.89 (br d, 1H, J=11.6 Hz), 2.6-2.6 (m, 1H), 2.2-2.3 (m, 1H), 1.8-2.0 (m, 3H) ppm. $^{13}$C NMR (CHLOROFORM-d, 101 MHz) δ 169.8, 167.6, 144.8, 135.6, 134.5, 128.6, 121.9, 78.2, 60.3, 57.8, 54.1, 47.5, 34.9, 20.7, 17.4 ppm.

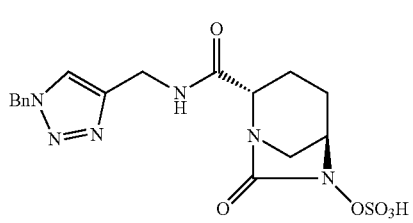

4.014

Using general procedure B 4.008 was converted to 4.014 (81%) to give a colorless oil. $^1$H NMR $^1$H NMR (DEUTERIUM OXIDE, 600 MHz) δ 7.84 (s, 1H), 7.3-7.4 (m, 2H), 7.2-7.3 (m, 1H), 5.53 (s, 2H), 4.5-4.5 (m, 1H), 4.4-4.4 (m, 1H), 4.0-4.1 (m, 1H), 3.96 (br d, 1H, J=7.6 Hz), 3.1-3.1 (m, 1H), 2.7-2.7 (m, 1H), 2.1-2.1 (m, 1H), 1.9-2.0 (m, 1H), 1.8-1.9 (m, 1H), 1.6-1.6 (m, 1H) ppm. HRMS m/z: [M-H]$^-$ calcd for C$_{17}$H$_{20}$N$_6$O$_6$S 436.1164; found 435.1091.

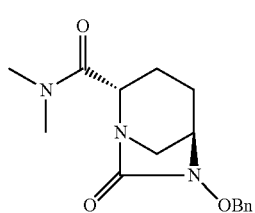

4.016

Using general procedure A, 4.001 and dimethylamine were converted to 4.016 (62%) to give a white solid. $^1$H NMR (CHLOROFORM-d, 400 MHz) δ 7.4-7.4 (m, 2H), 7.3-7.4 (m, 3H), 5.0-5.1 (m, 1H), 4.9-4.9 (m, 1H), 4.18 (br d, 1H, J=5.7 Hz), 3.31 (br s, 1H), 3.17 (s, 3H), 2.9-3.0 (m, 5H), 2.8-2.9 (m, 1H), 1.9-2.1 (m, 5H) ppm. $^{13}$C NMR (CHLOROFORM-d, 101 MHz) δ 169.8, 168.6, 135.8, 129.1, 128.6, 128.5, 78.1, 59.1, 57.7, 46.3, 37.6, 35.9, 20.9, 19.7 ppm.

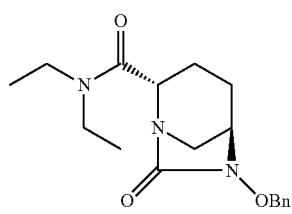

4.017

Using general procedure A, 4.001 and diethylamine were converted to 4.017 (78%) to give a white solid. $^1$H NMR (CHLOROFORM-d, 600 MHz) δ 7.3-7.4 (m, 3H), 7.3-7.3 (m, 4H), 4.97 (d, 1H, J=11.6 Hz), 4.84 (d, 1H, J=11.6 Hz), 4.08 (d, 1H, J=6.2 Hz), 3.64 (qd, 1H, J=7.2, 14.5 Hz), 3.4-3.5 (m, 1H), 3.3-3.3 (m, 1H), 3.26 (br s, 1H), 3.17 (qd, 1H, J=7.0, 13.8 Hz), 2.90 (d, 1H, J=11.3 Hz), 2.81 (br d, 1H, J=11.6 Hz), 1.8-2.0 (m, 5H), 1.0-1.1 (m, 6H) ppm. $^{13}$C NMR (CHLOROFORM-d, 151 MHz) δ 169.0, 168.7, 135.9, 129.2, 128.7, 128.5, 78.1, 59.2, 57.8, 46.1, 42.1, 40.2, 21.1, 19.9, 14.5, 12.8 ppm.

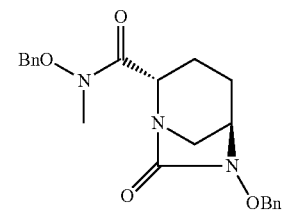

4.018

Using general procedure A, 4.001 and O-benzyl-N-methylhydroxylamine were converted to 4.018 (67%) to give a white solid. $^1$H NMR (CHLOROFORM-d, 600 MHz) δ 7.5-7.5 (m, 2H), 7.36 (br d, 2H, J=6.9 Hz), 7.3-7.3 (m, 7H), 5.13 (br d, 1H, J=8.4 Hz), 5.00 (br d, 2H, J=11.3 Hz), 4.8-4.9 (m, 3H), 4.60 (br s, 1H), 3.28 (br s, 2H), 3.22 (br d, 1H, J=11.3 Hz), 2.87 (br d, 1H, J=10.2 Hz), 1.9-2.0 (m, 1H), 1.8-1.9 (m, 2H), 1.7-1.8 (m, 1H) ppm.

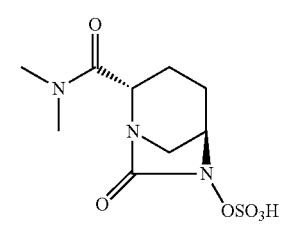

4.019

Using general procedure B, 4.006 was converted to 4.019 (80%) to give a white solid. HRMS m/z: [M-H]$^-$ calcd for C$_9$H$_{15}$N$_3$O$_6$S 293.0688; found 292.0615. $^1$H NMR (DEUTERIUM OXIDE, 600 MHz) δ 4.34 (br d, 2H, J=6.9 Hz), 4.15 (br s, 2H), 3.1-3.2 (m, 7H), 3.12 (br d, 3H, J=1.5 Hz), 2.90 (s, 5H), 2.0-2.0 (m, 1H), 1.9-2.0 (m, 2H), 1.8-1.9 (m, 1H) ppm.

4.020

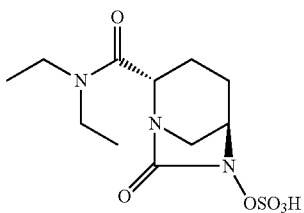

Using general procedure B, 4.017 was converted to 4.020 (85%) to give a white solid. ¹H NMR (DEUTERIUM OXIDE, 600 MHz) δ 4.09 (br d, 1H, J=6.5 Hz), 3.68 (br s, 1H), 3.62 (dt, 1H, J=6.7, 14.3 Hz), 3.46 (dt, 1H, J=7.1, 13.9 Hz), 3.3-3.3 (m, 1H), 3.15 (dt, 1H, J=6.9, 13.8 Hz), 3.0-3.1 (m, 1H), 1.8-2.0 (m, 4H), 1.1-1.2 (m, 6H), 1.04 (br t, 3H, J=7.1 Hz) ppm.

4.021

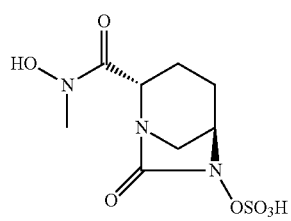

Using general procedure B, 4.018 was converted to 4.021 (58%) to give a pale yellow 4.022

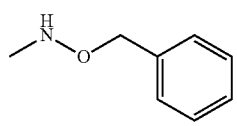

Compound 4.022 was synthesized using a known procedure to yield the product. ¹H NMR (CHLOROFORM-d, 600 MHz) δ 7.1-7.3 (m, 7H), 4.93 (br s, 2H), 2.79 (br s, 3H) ppm.

4.023

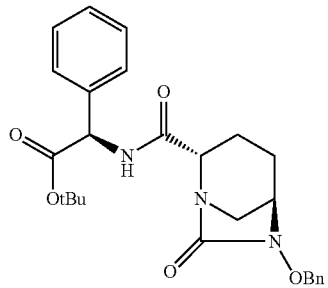

Using general procedure A, 4.001 and tert-butyl (R)-2-amino-2-phenylacetate were converted to 4.023 (72%) to give a white solid. ¹H NMR (CHLOROFORM-d, 600 MHz) δ 7.3-7.4 (m, 2H), 7.2-7.3 (m, 10H), 5.34 (d, 1H, J=7.6 Hz), 4.98 (d, 1H, J=11.3 Hz), 4.84 (d, 1H, J=11.6 Hz), 3.85 (d, 1H, J=7.6 Hz), 3.22 (br s, 1H), 3.04 (br d, 1H, J=11.6 Hz), 2.94 (d, 1H, J=11.6 Hz), 2.31 (dd, 1H, J=7.1, 15.1 Hz), 1.8-2.0 (m, 2H), 1.5-1.6 (m, 1H) ¹³C NMR (CHLOROFORM-d, 151 MHz) δ 169.7, 169.1, 167.6, 136.3, 135.7, 129.3, 129.0, 128.8, 128.6, 128.5, 127.3, 82.4, 78.3, 60.4, 57.9, 57.2, 47.9, 27.9, 20.9, 17.3 ppm.

4.025

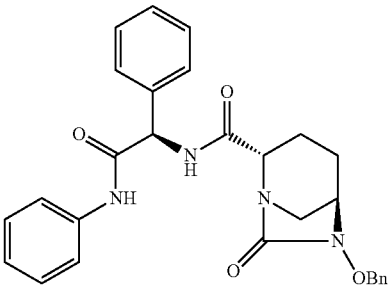

In a 5 mL round bottom flask was ester 4.023 (0.0500 g, 0.107 mmol) in DCM (0.200 mL). TFA (0.199 mL, 2.58 mmol) was added over 5 min at 10° C. The resulting solution was allowed to stir at room temperature and checked by TLC for completion. The solution was concentrated under reduced pressure with the addition of toluene to provide a residue. The residue was diluted in water and aqueous sodium bicarbonate solution. The solution was extracted with ethyl acetate. The organic layer was dried over MgSO₄, filtered, and concentrated under reduced pressure. The resulting solid (0.042 g, 95%) was used in the next step without further purification. Using general procedure A, the carboxylic acid and aniline were converted to 4.025 (83%) to give a white solid. ¹H NMR (CHLOROFORM-d, 600 MHz) δ 7.5-7.6 (m, 1H), 7.3-7.5 (m, 13H), 7.2-7.2 (m, 2H), 6.9-7.1 (m, 2H), 5.51 (d, 1H, J=7.3 Hz), 4.98 (d, 1H, J=11.6 Hz), 4.84 (d, 1H, J=11.6 Hz), 3.89 (br d, 1H, J=7.6 Hz), 3.1-3.3 (m, 2H), 3.0-3.1 (m, 1H), 3.00 (d, 1H, J=11.6 Hz), 2.30 (br dd, 2H, J=6.4, 14.7 Hz), 1.8-1.9 (m, 2H) ppm.

4.027

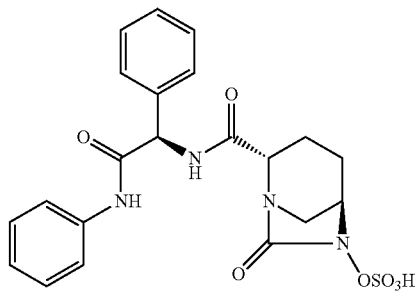

Using general procedure B 4.025 was converted to 4.027 (83%) to give a white solid. ¹H NMR (DEUTERIUM OXIDE, 600 MHz) δ 7.4-7.5 (m, 2H), 7.4-7.4 (m, 3H), 7.3-7.4 (m, 4H), 7.2-7.2 (m, 1H), 5.54 (s, 1H), 4.0-4.1 (m, 3H), 3.31 (br d, 1H, J=11.3 Hz), 3.21 (d, 1H, J=12.0 Hz), 2.14 (br dd, 1H, J=6.5, 15.3 Hz), 2.02 (br dd, 1H, J=3.8, 14.4 Hz), 1.8-1.9 (m, 1H), 1.7-1.8 (m, 1H) ppm. HRMS m/z. [M-H]⁻ calcd for $C_{21}H_{22}N_4O_7S$ 474.1211; found 473.1138.

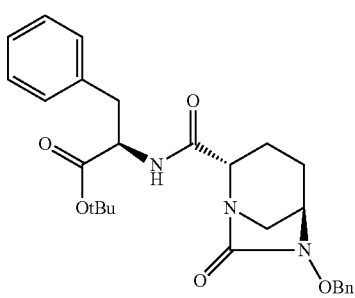

4.024

Using general procedure A, 4.001 and tert-butyl D-phenylalaninate were converted to 4.0024 (82%) to give a white solid.

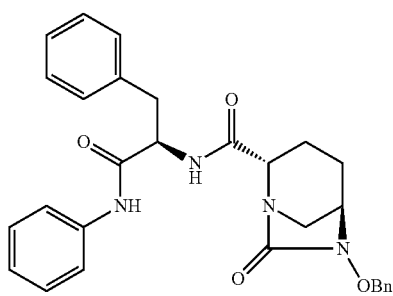

4.026

Using the same procedure as 4.025, 4.024 was converted to 4.026 (69%). $^1$H NMR (CHLOROFORM-d, 400 MHz) δ 7.3-7.4 (m, 2H), 7.3-7.3 (m, 3H), 7.23 (br d, 2H, J=7.8 Hz), 7.0-7.2 (m, 6H), 6.9-7.0 (m, 1H), 4.9-5.0 (m, 1H), 4.81 (d, 1H, J=11.3 Hz), 4.7-4.8 (m, 1H), 3.83 (br d, 1H, J=7.0 Hz), 3.0-3.1 (m, 2H), 2.95 (br dd, 2H, J=7.9, 13.9 Hz), 2.72 (d, 1H, J=12.0 Hz), 2.1-2.2 (m, 1H), 1.8-1.9 (m, 2H), 1.3-1.5 (m, 1H) ppm. $^{13}$C NMR (CHLOROFORM-d, 151 MHz) δ 170.5, 169.4, 167.6, 137.5, 136.3, 135.5, 129.3, 129.1, 128.9, 128.8, 128.8, 128.6, 127.2, 124.4, 120.0, 78.3, 60.1, 57.8, 55.8, 47.8, 38.4, 20.7, 17.6 ppm.

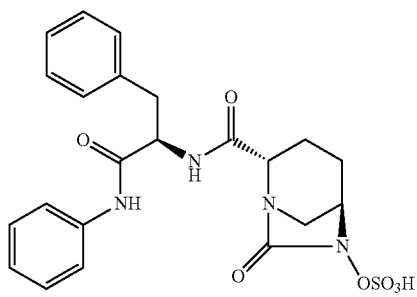

4.028

Using general procedure B, 4.026 was converted to 4.028 (89%) to give a white solid. $^1$H NMR (DEUTERIUM OXIDE, 600 MHz) δ 7.3-7.4 (m, 3H), 7.2-7.3 (m, 3H), 7.18 (br d, 6H, J=7.3 Hz), 4.65 (t, 1H, J=7.8 Hz), 4.09 (br d, 1H, J=1.8 Hz), 4.0-4.0 (m, 1H), 3.2-3.2 (m, 1H), 2.88 (d, 1H, J=12.0 Hz), 2.0-2.1 (m, 1H), 1.9-2.0 (m, 1H), 1.8-1.9 (m, 1H), 1.6-1.7 (m, 1H) ppm. HRMS m/z: [M-H]$^-$ calcd for C$_{22}$H$_{24}$N$_4$O$_7$S 488.1377; found 487.1304.

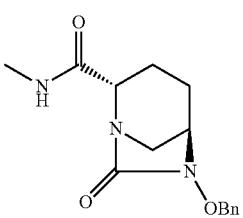

4.029

Using general procedure A, 4.001 and methylamine were converted to 4.029 (87%) to give a white solid. $^1$H NMR (CHLOROFORM-d, 600 MHz) δ 7.3-7.4 (m, 2H), 7.3-7.3 (m, 3H), 4.98 (d, 1H, J=11.3 Hz), 4.83 (d, 1H, J=11.6 Hz), 3.82 (br d, 1H, J=7.6 Hz), 3.2-3.3 (m, 1H), 2.8-3.0 (m, 1H), 2.77 (d, 3H, J=4.7 Hz), 2.63 (d, 1H, J=11.6 Hz), 2.30 (br dd, 1H, J=7.3, 14.9 Hz), 1.8-2.0 (m, 3H), 1.5-1.6 (m, 1H) ppm.

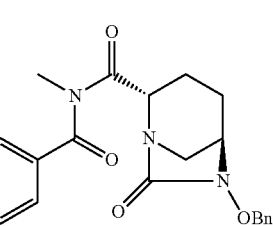

4.031

In a 10 mL round bottom flask was amide 4.029 (0.100 g, 0.346 mmol) in DCM (3.76 mL) and 4 A molecular sieves (1.56 g) Triethylamine (0.105 mL, 0.752 mmol) was added to the reaction and the reaction was cooled to 0° C. Benzoyl chloride (0.0602 mL, 0.518 mmol) was added at 0° C. and was allowed to warm up to room temperature and stir under argon overnight. The reaction mixture was filtered through celite and then organic layer was washed with water and brine. The organic layer was dried over MgSO$_4$, filtered, and concentrated under reduced pressure. The crude product was purified by flash chromatography on silica gel (hexanes-1:1 hexanes:ethyl acetate) to give compound 4.031 (0.0720 g, 53%) as a white solid. $^1$H NMR (CHLOROFORM-d, 600 MHz) δ 7.5-7.6 (m, 6H), 7.5-7.5 (m, 4H), 7.3-7.4 (m, 7H), 7.3-7.3 (m, 4H), 7.3-7.3 (m, 5H), 4.92 (d, 1H, J=11.3 Hz), 4.76 (d, 1H, J=11.6 Hz), 4.11 (br d, 1H, J=7.6 Hz), 4.05 (br dd, 1H, J=7.3, 14.2 Hz), 3.28 (s, 1H), 3.23 (s, 5H), 3.2-3.2 (m, 1H), 2.9-2.9 (m, 1H), 2.55 (d, 1H, J=11.3 Hz), 2.10 (s, 2H), 1.8-1.9 (m, 1H), 1.7-1.8 (m, 1H), 1.6-1.6 (m, 2H) ppm.

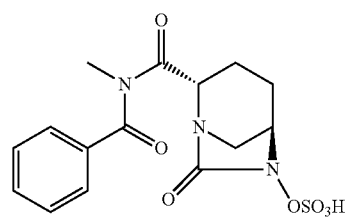

4.033

Using general procedure B, 4.031 was converted to 4.033 (75%) to give a white solid.

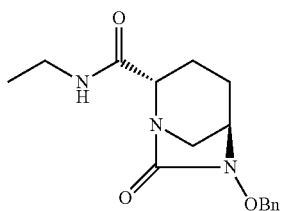
4.030

Using general procedure A, 4.001 and ethylamine were converted to 4.030 (95%) to give a white solid. ¹H NMR (CHLOROFORM-d, 600 MHz) δ 7.3-7.4 (m, 3H), 7.3-7.3 (m, 4H), 6.55 (br s, 1H), 4.99 (d, 2H, J=11.3 Hz), 4.84 (d, 1H, J=11.3 Hz), 3.82 (d, 1H, J=7.6 Hz), 3.2-3.4 (m, 4H), 2.9-3.0 (m, 2H), 2.63 (d, 1H, J=11.3 Hz), 2.32 (br dd, 1H, J=7.1, 15.1 Hz), 1.8-2.0 (m, 3H), 1.53 (dddd, 1H, J=1.8, 7.4, 9.9, 13.9 Hz), 1.06 (t, 3H, J=7.3 Hz) ppm.

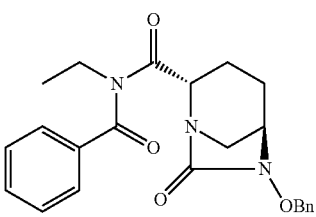
4.032

Compound 4.032 was synthesized using the same procedure as 4.032 (59%) to give a white solid. ¹³C NMR (CHLOROFORM-d, 151 MHz) δ 173.4, 172.0, 166.0, 134.7, 132.7, 131.7, 129.2, 128.2, 128.0, 127.6, 127.5, 127.5, 77.2, 58.9, 56.9, 40.9, 28.7, 19.8, 17.4, 13.1 ppm.

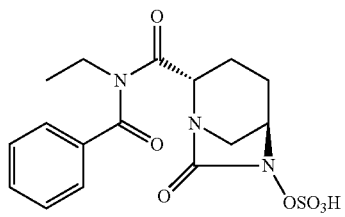
4.034

Using general procedure B 4.031 was converted to 4.034 (83%) to give a white solid. [M-H]⁻ calcd for C₁₆H₁₉N₃O₇S 397.0926; found 396.0852.

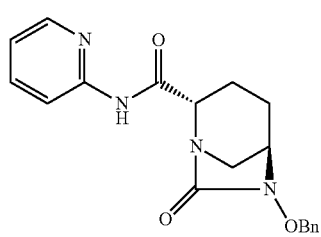
4.035

Using general procedure A, 4.001 and pyridin-2-amine were converted to 4.035 (88%) to give a white solid. ¹H NMR (CHLOROFORM-d, 400 MHz) δ 8.2-8.3 (m, 2H), 8.11 (d, 2H, J=8.3 Hz), 7.64 (dt, 2H, J=2.0, 7.9 Hz), 7.3-7.4 (m, 7H), 6.99 (ddd, 1H, J=1.0, 4.9, 7.3 Hz), 5.01 (d, 1H, J=11.3 Hz), 4.86 (d, 1H, J=11.5 Hz), 4.0-4.1 (m, 1H), 3.2-3.3 (m, 1H), 3.0-3.1 (m, 1H), 2.68 (d, 1H, J=11.8 Hz), 2.3-2.4 (m, 1H), 1.9-2.0 (m, 3H), 1.5-1.6 (m, 1H) ppm. ¹³C NMR (CHLOROFORM-d, 101 MHz) δ 168.5, 150.8, 148.1, 138.4, 135.6, 129.3, 128.9, 128.6, 120.1, 113.8, 78.4, 61.2, 57.8, 47.8, 20.8, 17.1 ppm.

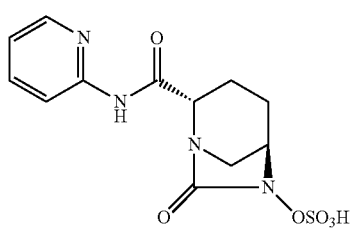
4.040

Using general procedure B 4.035 was converted to 4.040 (86%) to give a white solid. ¹³C NMR (DEUTERIUM OXIDE, 151 MHz) δ 170.4, 169.0, 149.5, 147.7, 139.6, 121.5, 116.3, 60.9, 59.6, 47.1, 19.7, 17.7 ppm. HRMS m/z: [M-H]⁻ calcd for C₁₂H₁₄N₄O₆S 342.0638; found 341.0565.

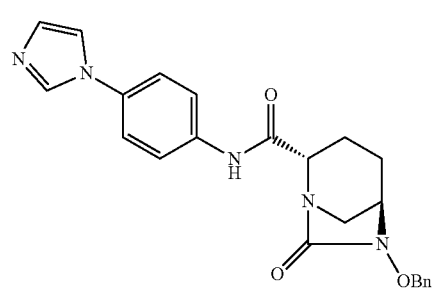
4.036

Using general procedure A, 4.001 and 4-(1H-imidazol-1-yl)aniline were converted to 4.036 (83%) to give a white solid. ¹H NMR (CHLOROFORM-d, 600 MHz) δ 8.58 (s, 1H), 7.76 (s, 1H), 7.61 (br d, 3H, J=7.6 Hz), 7.4-7.4 (m, 2H), 7.3-7.3 (m, 5H), 7.19 (br s, 1H), 7.14 (br s, 2H), 5.01 (d, 2H, J=11.6 Hz), 4.87 (d, 1H, J=11.6 Hz), 4.0-4.1 (m, 1H), 3.31 (br s, 1H), 3.04 (br d, 1H, J=11.3 Hz), 2.71 (d, 1H, J=11.3 Hz), 2.39 (br dd, 2H, J=7.1, 14.7 Hz), 1.9-2.0 (m, 3H) ppm. ¹³C NMR (CHLOROFORM-d, 151 MHz) δ 168.0, 167.2, 133.7, 130.4, 129.3, 129.0, 128.7, 122.3, 120.6, 118.4, 78.4, 61.1, 57.7, 47.8, 20.7, 17.0 ppm.

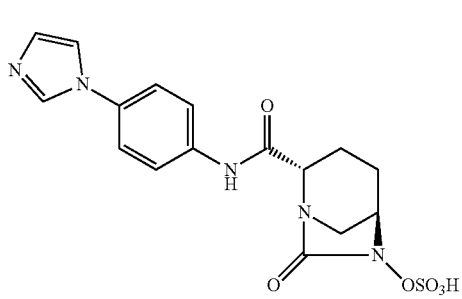

4.041

Using general procedure B 4.036 was converted to 4.041 (77%) to give a white solid.

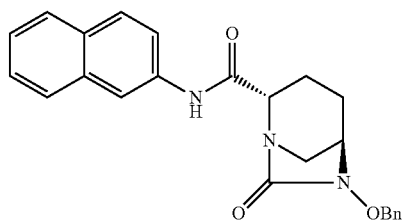

4.037

Using general procedure A, 4.001 and naphthalen-2-amine were converted to 4.037 (80%) to give a white solid. ¹H NMR (CHLOROFORM-d, 600 MHz) δ 8.55 (br s, 1H), 8.19 (s, 1H), 7.6-7.8 (m, 3H), 7.4-7.4 (m, 3H), 7.2-7.4 (m, 4H), 5.02 (d, 1H, J=11.3 Hz), 4.88 (d, 1H, J=11.3 Hz), 4.0-4.1 (m, 1H), 3.30 (br s, 1H), 3.05 (br d, 1H, J=11.6 Hz), 2.75 (d, 1H, J=11.6 Hz), 2.44 (br dd, 1H, J=7.3, 14.2 Hz), 1.9-2.1 (m, 2H), 1.6-1.6 (m, 1H) ppm. ¹³C NMR (CHLOROFORM-d, 151 MHz) δ 167.9, 167.3, 135.6, 134.9, 133.8, 130.7, 129.3, 128.9, 128.9, 128.7, 127.7, 127.6, 126.7, 125.2, 119.4, 116.2, 78.4, 61.2, 57.8, 47.9, 20.8, 17.1 ppm.

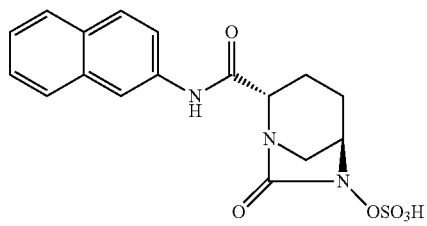

4.042

Using general procedure B 4.031 was converted to 4.042 (83%) to give a white solid. ¹H NMR (DEUTERIUM OXIDE, 600 MHz) δ 7.8-7.9 (m, 2H), 7.7-7.8 (m, 5H), 7.3-7.4 (m, 5H), 4.0-4.1 (m, 2H), 3.95 (br d, 2H, J=7.6 Hz), 3.18 (br d, 2H, J=11.6 Hz), 2.93 (d, 1H, J=12.0 Hz), 2.09 (br dd, 1H, J=6.7, 15.4 Hz), 1.94 (td, 1H, J=3.3, 11.2 Hz), 1.7-1.8 (m, 1H), 1.6-1.7 (m, 1H) ppm. ¹³C NMR (DEUTERIUM OXIDE, 151 MHz) δ 170.3, 169.2, 134.0, 133.1, 130.9, 128.8, 127.6, 127.6, 126.8, 125.9, 121.4, 119.0, 60.8, 59.7, 47.0, 19.8, 17.9 ppm. HRMS m/z: [M-H]⁻ calcd for $C_{17}H_{17}N_3O_6S$ 391.083; found 390.0757.

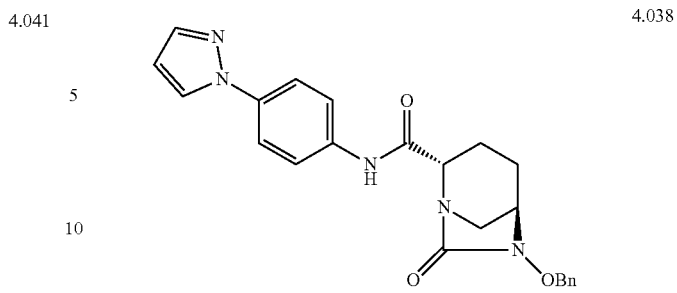

4.038

Using general procedure A, 4.001 and 4-(1H-pyrazol-1-yl)aniline were converted to 4.036 (91%) to give a white solid. ¹H NMR (CHLOROFORM-d, 600 MHz) δ 8.51 (s, 2H), 7.8-7.9 (m, 2H), 7.6-7.7 (m, 2H), 7.58 (s, 5H), 7.3-7.4 (m, 3H), 7.3-7.3 (m, 4H), 6.38 (s, 1H), 5.00 (d, 1H, J=11.6 Hz), 4.86 (d, 1H, J=11.6 Hz), 4.0-4.1 (m, 1H), 3.29 (br s, 1H), 3.02 (br d, 1H, J=11.6 Hz), 2.72 (d, 1H, J=11.6 Hz), 2.38 (br dd, 1H, J=7.3, 14.9 Hz), 1.9-2.0 (m, 3H), 1.6-1.6 (m, 1H) ppm. ¹³C NMR (CHLOROFORM-d, 151 MHz) δ 167.8, 167.3, 141.0, 136.6, 135.9, 135.5, 129.3, 128.9, 128.7, 126.7, 120.3, 119.9, 107.6, 78.4, 61.1, 57.7, 47.8, 20.7, 17.1 ppm.

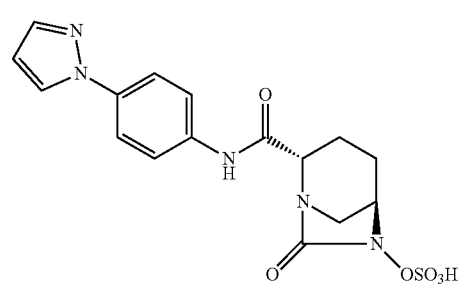

4.043

Using general procedure B 4.031 was converted to 4.043 (83%) to give a white solid. ¹H NMR (DEUTERIUM OXIDE, 600 MHz) δ 7.97 (d, 1H, J=2.2 Hz), 7.63 (d, 1H, J=1.5 Hz), 7.4-7.5 (m, 3H), 7.40 (d, 3H, J=8.7 Hz), 6.42 (t, 1H, J=2.2 Hz), 4.0-4.1 (m, 1H), 4.01 (br d, 1H, J=6.9 Hz), 3.22 (br d, 1H, J=12.0 Hz), 2.99 (d, 1H, J=12.0 Hz), 2.1-2.2 (m, 1H), 1.9-2.0 (m, 1H), 1.8-1.9 (m, 1H), 1.70 (br d, 1H, J=7.3 Hz) ppm. 13C NMR (DEUTERIUM OXIDE, 151 MHz) δ 170.3, 169.2, 141.5, 136.6, 135.2, 129.0, 122.9, 120.1, 107.8, 60.8, 59.7, 47.0, 19.8, 17.9 ppm. HRMS m/z: [M-H]⁻ calcd for $C_{16}H_{17}N_5O_6S$ 407.0906; found 406.0833.

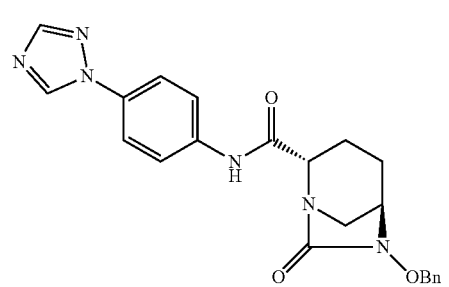

4.039

Using general procedure A, 4.001 4-(1H-1,2,4-triazol-1-yl)aniline were converted to 4.036 (87%) to give a white solid. ¹H NMR (400 MHz) δ 9.02 (s, 1H), 8.16 (s, 1H), 7.64 (dd, 1H, J=2.7, 8.8 Hz), 7.64 (dd, 1H, J=2.7, 8.8 Hz), 7.59 (d, 1H, J=8.8 Hz), 7.59 (d, 1H, J=8.8 Hz), 7.41 (d, 1H, J=7.4 Hz), 7.41 (d, 1H, J=7.4 Hz), 7.33 (t, 1H, J=7.4 Hz), 7.31 (t, 1H, J=7.4 Hz), 7.31 (t, 1H, J=7.4 Hz), 5.01 (d, 1H, J=10.1 Hz), 4.94 (d, 1H, J=10.1 Hz), 4.19 (dd, 1H, J=6.1, 8.2 Hz), 3.80 (d, 1H, J=11.5 Hz), 3.69 (dt, 1H, J=2.8, 5.7 Hz), 3.29 (dd, 1H, J=2.8, 11.5 Hz), 2.10 (dtd, 1H, J=6.1, 13.4, 13.9 Hz), 1.99 (ddt, 1H, J=5.7, 13.2, 13.4 Hz), 1.68 (ddt, 1H, J=5.7, 13.2, 13.4 Hz), 1.41 (dtd, 1H, J=8.2, 13.4, 13.9 Hz) ppm. ¹³C NMR (CHLOROFORM-d, 101 MHz) δ 168.1, 167.3, 152.5, 140.8, 137.6, 135.5, 133.1, 129.3, 128.9, 128.7, 120.9, 120.4, 78.4, 61.1, 57.7, 47.7, 20.7, 17.1 ppm.

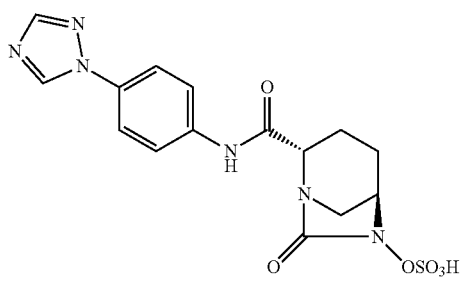

4.044

Using general procedure B 4.031 was converted to 4.033 (73%) to give a white solid. ¹H NMR (DEUTERIUM OXIDE, 600 MHz) δ 8.8-8.9 (m, 1H), 8.1-8.2 (m, 1H), 7.7-7.7 (m, 2H), 7.6-7.7 (m, 1H), 4.2-4.2 (m, 1H), 3.3-3.4 (m, 1H), 3.1-3.2 (m, 1H), 2.2-2.3 (m, 1H), 2.0-2.1 (m, 1H), 1.9-2.0 (m, 1H), 1.8-1.8 (m, 1H) HRMS m/z: [M-H]⁻ calcd for $C_{15}H_{16}N_6O_6S$ 408.0839; found 407.0766.

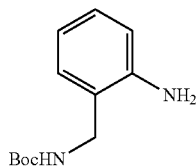

4.045

Compound 4.045 was synthesized by a known route from 2-(aminomethyl)aniline (78%). ¹³C NMR (CHLOROFORM-d, 151 MHz) δ 156.5, 145.4, 130.3, 129.1, 122.6, 117.9, 115.8, 79.8, 42.1, 28.4 ppm.

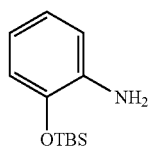

4.046

Compound 4.046 was synthesized using a known procedure (73%).

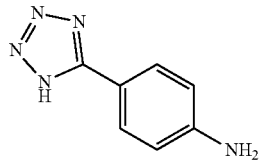

4.047

Compound 4-aminobenzonitrile (0.200 g, 1.69 mmol) was dissolved in toluene (223 μL). Azidotributyltin (2.41 mL, 8.80 mmol) was added to the reaction. The resulting mixture was refluxed for 48 hours. The reaction was cooled to room temperature, acidified to pH with HCl, and then extracted with EtOAc. The organic layer was dried over magnesium sulfate, filtered, and concentrated under reduced pressure to give the product as a tan solid (0.260 g, 95%).

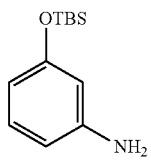

4.048

Compound 4.048 was synthesized using the same procedure as 4.046. (70%). ¹H NMR (CHLOROFORM-d, 600 MHz) δ 6.81 (t, 1H, J=8.0 Hz), 6.0-6.1 (m, 2H), 6.01 (t, 1H, J=2.4 Hz), 0.79 (s, 9H), 0.0-0.0 (m, 6H) ppm.

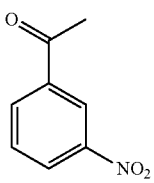

4.049

Compound 4.049 was synthesized using a known procedure. (46%)¹H NMR (CHLOROFORM-d, 400 MHz) δ 7.7-7.9 (m, 1H), 7.4-7.5 (m, 2H), 7.2-7.3 (m, 2H), 2.11 (s, 5H) ppm.

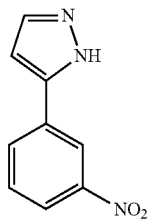

4.050

Compound 4.049 (0.500 g, 3.03 mmol) was dissolved in DMF-DMA (13.2 mL). The reaction was heated at 110° C. to form a yellow slurry. After cooling, the solvent was removed under reduced pressure and the crude solid (0.505 g, 96%) was used in the next step without further purification.

The crude product (0.100 g, 0.454 mmol) was dissolved in 0.927 mL of ethanol. The reaction was cooled in an ice bath and hydrazine hydrate (0.131 mL, 1.60 mmol) was added dropwise while stirring. After the addition was complete, the reaction warmed to room temperature and stirred overnight. Water was added to the reaction and the reaction was concentrated under reduced pressure until the ethanol was removed. The water was extracted with ethyl acetate, dried over magnesium sulfate, and concentrated under reduced pressure to give the product (0.0391 g, 45%). $^1$H NMR (CHLOROFORM-d, 400 MHz) δ 8.57 (t, 1H, J=1.9 Hz), 8.1-8.1 (m, 2H), 7.64 (d, 1H, J=2.3 Hz), 7.5-7.5 (m, 1H), 6.67 (d, 1H, J=2.3 Hz) ppm.

4.051

Compound 4.051 (0.250 g, 1.32 mmol) was dissolved in degassed methanol (7.91 mL) and placed in an argon flushed round-bottomed flask. Palladium on carbon (0.0281 g, 0.026 mmol) and ammonium formate (0.333 g, 5.29 mmol) were added to the reaction. The reaction was heated overnight. The reaction was cooled to room temperature and filtered through a pad of celite. The ethanol was removed to give the crude product (0.202 g, 96%). The product was used in the next step without further purification.

4.055

Compound 3-nitroaniline (0.500 g, 3.62 mmol) was dissolved in acetic acid (3.47 mL). The reaction was diluted with water (3.47 mL). Potassium cyanate (0.587 g, 7.24 mmol) in warm water (3.26 mL) was added with continuous stirring. The mixture was warmed to 50° C. for 2 hours then cooled in ice. The crude solid was filtered and recrystallized in water to give the nitro urea product (0.354 g, 54%). $^1$H NMR (METHANOL-d$_4$, 600 MHz) δ 8.47 (t, 1H, J=2.0 Hz), 7.8-7.9 (m, 1H), 7.6-7.7 (m, 1H), 7.49 (t, 1H, J=8.2 Hz) ppm. $^{13}$C NMR (METHANOL-d$_4$, 151 MHz) δ 157.4, 148.6, 141.2, 129.3, 123.9, 116.2, 112.7 ppm.

4.056

Compound 4.056 was synthesized using the same procedure as 4.051. (93%)

4.057

Using general procedure A, 4.001 and 4.045 were used to synthesize 4.057 (92%). $^1$H NMR (CHLOROFORM-d, 400 MHz) δ 7.78 (br d, 1H, J=8.0 Hz), 7.2-7.4 (m, 9H), 7.0-7.1 (m, 1H), 4.98 (d, 1H, J=11.5 Hz), 4.83 (d, 2H, J=11.5 Hz), 4.2-4.4 (m, 1H), 4.0-4.2 (m, 3H), 3.2-3.3 (m, 1H), 3.12 (br d, 1H, J=11.5 Hz), 2.78 (d, 1H, J=11.5 Hz), 2.3-2.4 (m, 1H), 1.9-2.1 (m, 3H), 1.55 (br dd, 1H, J=1.9, 6.9 Hz), 1.36 (s, 9H) ppm. $^{13}$C NMR (CHLOROFORM-d, 101 MHz) δ 168.7, 167.6, 156.1, 135.7, 135.6, 130.0, 129.3, 128.8, 128.8, 128.6, 125.4, 123.5, 78.3, 61.1, 57.9, 47.6, 42.2, 28.3, 20.8, 17.6 ppm.

4.058

Using general procedure A, 4.001 and 4.046 were used to synthesize 4.058 (85%). $^1$H NMR (CHLOROFORM-d, 400 MHz) δ 8.2-8.4 (m, 2H), 7.3-7.4 (m, 7H), 6.8-6.9 (m, 3H), 6.7-6.8 (m, 2H), 5.0-5.1 (m, 1H), 4.86 (d, 1H, J=11.5 Hz), 4.0-4.1 (m, 1H), 3.1-3.5 (m, 2H), 2.95 (br d, 1H, J=11.5 Hz), 2.71 (d, 1H, J=11.5 Hz), 2.2-2.5 (m, 2H), 1.8-2.1 (m, 3H), 0.96 (s, 9H), 0.21 (d, 7H, J=5.5 Hz) ppm. $^{13}$C NMR (CHLOROFORM-d, 101 MHz) δ 167.6, 167.4, 144.2, 135.7, 129.3, 128.8, 128.6, 123.8, 121.6, 119.6, 117.6, 78.3, 61.4, 57.8, 47.7, 29.7, 25.7, 20.8, 17.2, −4.1, −4.4 ppm.

4.059

Using general procedure A, 4.001 and 4.047 were used to synthesize 4.059 (76%). $^{13}$C NMR (ACETONITRILE-d$_3$, 101 MHz) δ 129.7, 128.9, 128.8, 128.1, 120.4, 77.8, 61.1, 57.4, 47.7, 20.7, 17.8 ppm.

4.060

Using general procedure A, 4.001 and 4.048 were used to synthesize 4.060 (94%). $^1$H NMR (CHLOROFORM-d, 400 MHz) δ 7.1-7.3 (m, 8H), 6.9-7.0 (m, 3H), 6.8-6.9 (m, 2H), 6.40 (ddd, 2H, J=0.9, 2.3, 8.1 Hz), 4.87 (d, 2H, J=11.5 Hz), 4.73 (d, 2H, J=11.3 Hz), 3.85 (d, 2H, J=7.3 Hz), 3.0-3.2 (m, 2H), 2.87 (br d, 2H, J=11.5 Hz), 2.55 (d, 2H, J=11.5 Hz), 2.2-2.3 (m, 2H), 1.7-1.9 (m, 3H), 1.4-1.5 (m, 1H), 0.7-0.8 (m, 9H), 0.00 (s, 6H) ppm. $^{13}$C NMR (CHLOROFORM-d, 101 MHz) δ 167.6, 156.3, 138.5, 135.5, 129.7, 129.3, 128.9, 128.7, 116.2, 112.2, 111.4, 78.4, 61.1, 57.8, 47.8, 25.7, 20.8, 17.0, 1.1, −4.4 ppm.

4.061

Using general procedure A, 4.001 and 4.051 were used to synthesize 4.061 (81%). $^1$H NMR (CHLOROFORM-d, 400 MHz) δ 8.55 (s, 1H), 7.97 (s, 1H), 7.5-7.8 (m, 1H), 7.4-7.5 (m, 2H), 7.3-7.4 (m, 6H), 4.9-5.1 (m, 1H), 4.87 (d, 1H, J=11.5 Hz), 4.0-4.1 (m, 2H), 3.2-3.4 (m, 2H), 3.04 (br d, 2H, J=11.5 Hz), 2.7-2.7 (m, 2H), 2.40 (br dd, 2H, J=6.4, 14.4 Hz), 1.9-2.1 (m, 3H) ppm.

4.063

Using general procedure A, 4.001 and 4.056 were used to synthesize 4.063 (90%). $^1$H NMR (CHLOROFORM-d, 400 MHz) δ 8.47 (s, 2H), 7.4-7.6 (m, 2H), 7.3-7.4 (m, 6H), 7.18 (br s, 1H), 7.0-7.1 (m, 1H), 6.92 (br d, 1H, J=6.8 Hz), 4.9-5.1 (m, 2H), 4.86 (d, 2H, J=11.3 Hz), 3.98 (br d, 1H, J=7.3 Hz), 3.30 (br s, 2H), 3.01 (br d, 1H, J=11.3 Hz), 2.69 (d, 1H, J=11.5 Hz), 2.3-2.4 (m, 1H), 1.8-2.0 (m, 4H) ppm. $^{13}$C NMR (CHLOROFORM-d, 101 MHz) δ 168.0, 167.4, 156.3, 139.2, 138.2, 135.4, 129.9, 129.3, 129.0, 128.7, 116.6, 114.9, 111.7, 78.4, 57.8, 47.7, 20.7, 17.2 ppm.

4.064

Using general procedure B 4.057 was converted to 4.064 (77%) to give a yellow oil. The product was used in the next step without further purification.

4.065

Using general procedure B 4.058 was converted to 4.065 (82%) to give a light tan solid. The product was used in the next step without further purification.

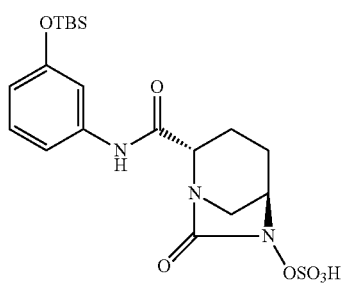

4.067

Using general procedure B 4.060 was converted to 4.067 (73%) to give a light tan solid. The product was used in the next step without further purification.

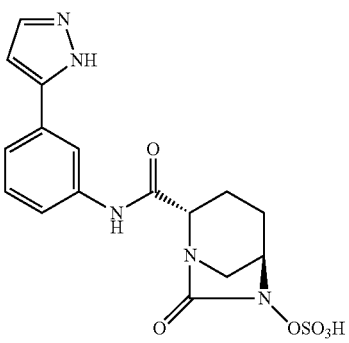

4.068

Using general procedure B 4.061 was converted to 4.068 (80%) to give a white solid. ¹H NMR (DEUTERIUM OXIDE, 600 MHz) δ 7.6-7.8 (m, 2H), 7.5-7.6 (m, 1H), 7.3-7.4 (m, 2H), 6.63 (br s, 1H), 4.0-4.1 (m, 2H), 3.2-3.3 (m, 1H), 2.1-2.2 (m, 1H), 2.0-2.0 (m, 1H), 1.8-1.9 (m, 1H), 1.7-1.8 (m, 1H) ppm. HRMS m/z: [M-H]⁻ calcd for $C_{16}H_{17}N_5O_6S$ 407.0894; found 406.0822.

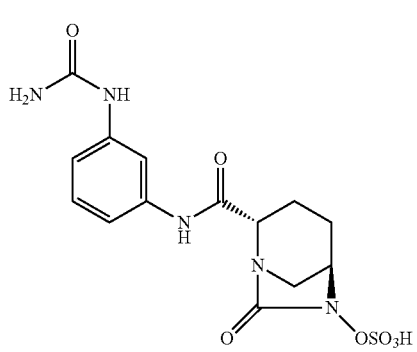

4.070

Using general procedure B 4.063 was converted to 4.070 (74%) to give a white solid. ¹H NMR (DEUTERIUM OXIDE, 600 MHz) δ 7.3-7.5 (m, 3H), 7.3-7.3 (m, 2H), 7.1-7.2 (m, 2H), 7.10 (br d, 2H, J=8.0 Hz), 4.1-4.2 (m, 1H), 4.12 (br d, 1H, J=7.6 Hz), 3.30 (br d, 2H, J=12.0 Hz), 3.1-3.1 (m, 1H), 2.1-2.3 (m, 2H), 2.0-2.1 (m, 1H), 1.8-2.0 (m, 1H), 1.7-1.8 (m, 1H) ppm. ¹³C NMR (DEUTERIUM OXIDE, 151 MHz) δ 170.4, 169.2, 138.6, 137.1, 129.7, 118.6, 117.7, 114.9, 60.9, 59.8, 47.0, 23.7, 19.8, 18.0 ppm. HRMS m/z: [M-H]⁻ calcd for $C_{14}H_{17}N_5O_7S$ 399.0853; found 398.0773.

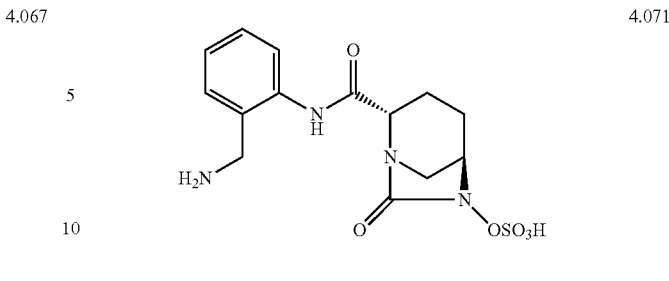

4.071

Compound 4.064 (66.6 mg, 0.142 mmol) was dissolved in water (1.16 mL) and heated to reflux until completion. The reaction was monitored by TLC. The product was purified by reverse phase preparative HPLC to give the product (46%) as a white solid. HRMS m/z: [M-H]⁻ calcd for $C_{14}H_{18}N_4O_6S$ 370.093; found 369.0585.

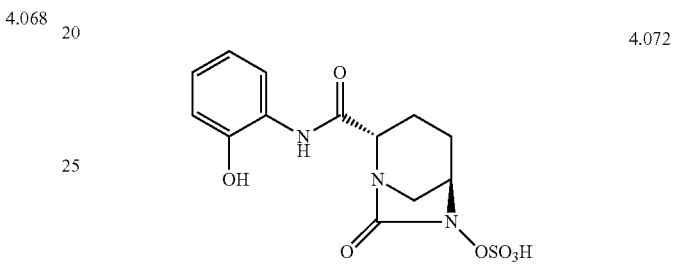

4.072

Compound 4.065 (135 mg, 0.286 mmol) was dissolved in THF (6.50 mL) and cooled to 0° C. Tetrabutylammonium fluoride hydrate (80.0 mg, 0.286 mmol) was added to the reaction. The reaction stirred until completion and the product was purified by reverse phase preparative HPLC to give the product (88%) as a clear oil. ¹H NMR (DEUTERIUM OXIDE, 600 MHz) δ 7.5-7.7 (m, 1H), 7.1-7.2 (m, 1H), 6.9-7.0 (m, 2H), 4.1-4.2 (m, 2H), 4.0-4.1 (m, 1H), 3.3-3.4 (m, 1H), 3.17 (dd, 1H, J=2.2, 12.0 Hz), 2.27 (br dd, 1H, J=6.4, 14.7 Hz), 2.05 (dt, 1H, J=2.9, 7.1 Hz), 1.9-2.0 (m, 1H), 1.8-1.9 (m, 1H) ppm. HRMS m/z: [M-H]⁻ calcd for $C_{13}H_{15}N_3O_7S$ 357.064; found 356.0567.

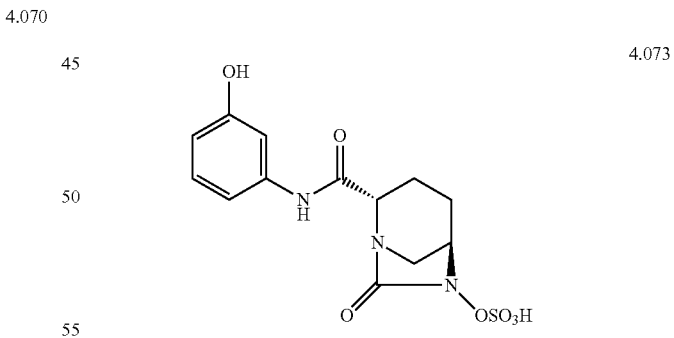

4.073

Compound 4.073 was synthesized using the same conditions as 4.072 to yield the product as a clear oil (96%). ¹H NMR (DEUTERIUM OXIDE, 600 MHz) δ 7.2-7.3 (m, 1H), 7.02 (s, 1H), 6.96 (br d, 1H, J=8.0 Hz), 6.7-6.7 (m, 1H), 4.18 (br d, 1H, J=2.2 Hz), 4.15 (br d, 1H, J=7.6 Hz), 4.0-4.1 (m, 1H), 3.95 (td, 1H, J=6.3, 12.4 Hz), 3.33 (br d, 1H, J=12.0 Hz), 2.2-2.3 (m, 1H), 2.0-2.1 (m, 1H), 1.9-2.0 (m, 1H), 1.8-1.8 (m, 1H) ppm. HRMS m/z: [M-H]⁻ calcd for $C_{13}H_{15}N_3O_7S$ 357.0632; found 356.0559.

Other advantages which are obvious, and which are inherent to the invention, will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods and compositions of the appended claims are not limited in scope by the specific methods and compositions described herein, which are intended as illustrations of a few aspects of the claims and any methods and compositions that are functionally equivalent are intended to fall within the scope of the claims. Various modifications of the methods and compositions in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

REFERENCES

Control, C. f. D. & Prevention. *Antibiotic resistance threats in the United States,* 2019. (US Department of Health and Human Services, Centres for Disease Control and . . . , 2019).

Paredes-Sabja, D., Shen, A. & Sorg, J. A. *Clostridium difficile* spore biology: sporulation, germination, and spore structural proteins. *Trends in microbiology* 22, 406-416 (2014).

Dembek, M. et al. High-throughput analysis of gene essentiality and sporulation in *Clostridium difficile*. *MBio* 6 (2015).

What is claimed is:

1. A compound represented by the formula:

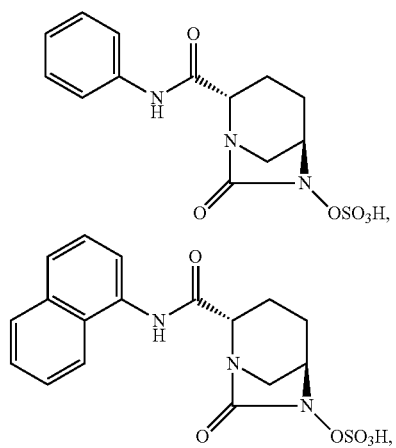

2. The compound of claim 1, wherein the compound is represented by the formula:

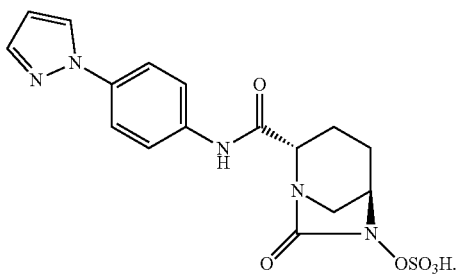

3. The compound of claim 1, wherein the compound is represented by:

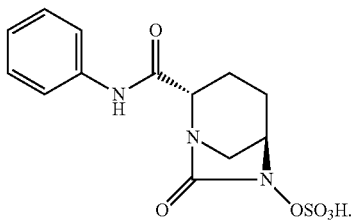

4. The compound of claim 1, wherein the compound is represented by:

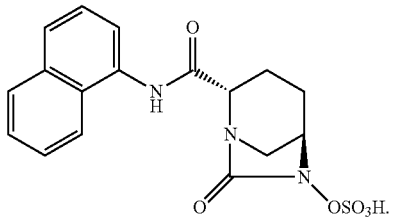

5. The compound of claim 1, wherein the compound is represented by:

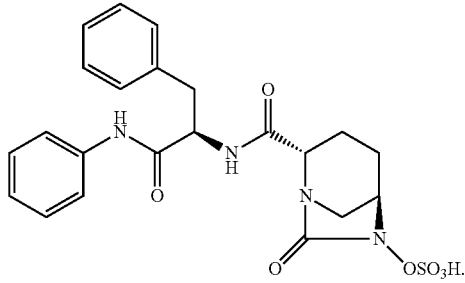

Spo10

6. A pharmaceutical composition, comprising the compound of claim 1 and an antibiotic.

7. A formulation, comprising the compound of claim 1 and a pharmaceutically acceptable excipient.

8. A method of preventing and treating *C. difficile*, infection comprising administering to a patient in need thereof a therapeutically effective amount of the compound of claim 1.

9. A compound represented by the formula:

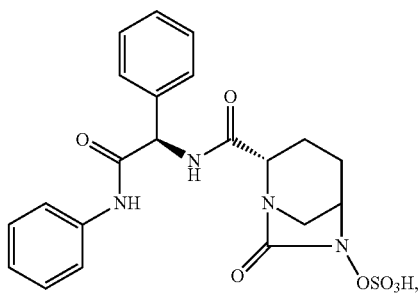

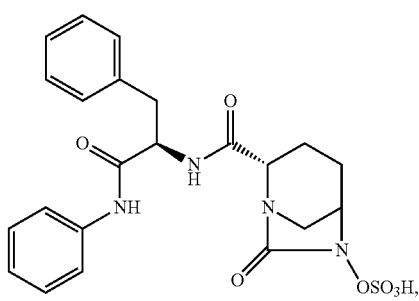

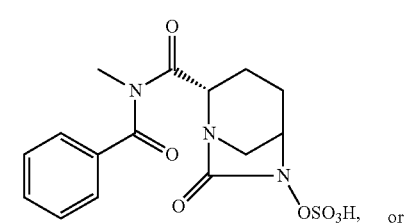

or

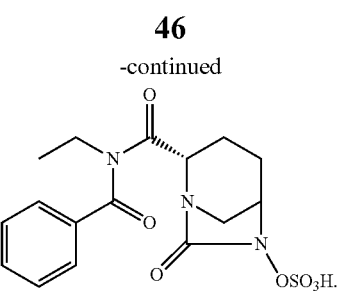

10. The compound of claim 9, wherein the compound is represented by:

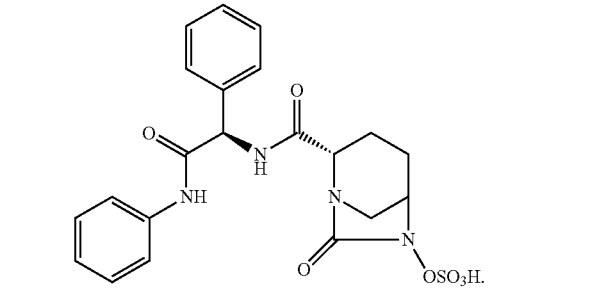

4.027

11. The compound of claim 9, wherein the compound is represented by:

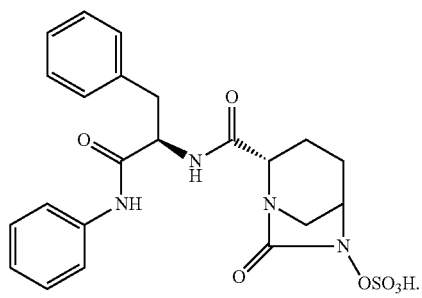

4.028

12. The compound of claim 9, wherein the compound is represented by:

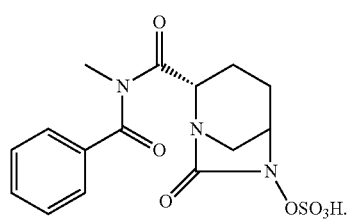

4.033

13. The compound of claim 9, wherein the compound is represented by:

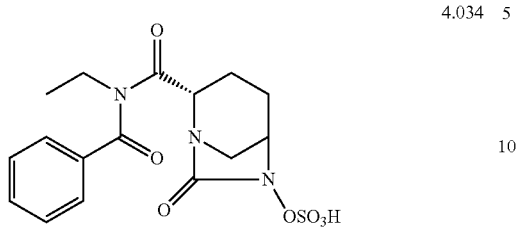

14. A pharmaceutical composition, comprising the compound of claim 9 and an antibiotic.

15. A formulation, comprising the compound of claim 9 and a pharmaceutically acceptable excipient.

16. A method of preventing and treating *C. difficile*, infection comprising administering to a patient in need thereof a therapeutically effective amount of the compound of claim 9.

* * * * *